United States Patent [19]
Mazer et al.

[11] Patent Number: 5,698,222
[45] Date of Patent: Dec. 16, 1997

[54] CALCIUM SUPPLEMENT

[75] Inventors: Terrence Bruce Mazer, Reynoldsburg; Normanella Torres DeWille, Columbus; Michael Allen Chandler; Robert John Ragan, both of Gahanna; Gregory Allan Snowden, Westerville; Maureen Elizabeth Geraghty, Columbus; Catherine Dubinin Johnson, Dublin; Lonnie Richard Drayer, Gahanna, all of Ohio

[73] Assignee: Abbott Laboratories, Abbott Park, Ill.

[21] Appl. No.: 418,393

[22] Filed: Apr. 7, 1995

[51] Int. Cl.⁶ .................................................. A61K 9/20
[52] U.S. Cl. .................... 424/464; 424/439; 424/500; 424/682; 514/904; 514/905
[58] Field of Search ........................... 514/310, 904, 514/905; 426/73; 424/439, 464, 500, 682

[56] References Cited

U.S. PATENT DOCUMENTS

| | | | |
|---|---|---|---|
| 3,949,098 | 4/1976 | Bangert | 426/324 |
| 4,252,797 | 2/1981 | Rosenthal | 514/52 |
| 4,737,375 | 4/1988 | Nakel et al. | 426/590 |
| 4,740,380 | 4/1988 | Melachuris et al. | 426/590 |
| 4,786,510 | 11/1988 | Nakel et al. | 426/76 |
| 4,867,989 | 9/1989 | Silva et al. | 426/5 |
| 4,956,191 | 9/1990 | Ueda et al. | 426/330.3 |
| 4,992,282 | 2/1991 | Mehansho et al. | 426/72 |
| 5,158,944 | 10/1992 | Makino et al. | 514/167 |
| 5,221,668 | 6/1993 | Henningfield et al. | 514/23 |
| 5,260,279 | 11/1993 | Greenberg | 514/21 |
| 5,401,524 | 3/1995 | Burkes et al. | 426/590 |
| 5,438,042 | 8/1995 | Schmidl et al. | 514/21 |
| 5,456,926 | 10/1995 | Hill et al. | 426/73 |

FOREIGN PATENT DOCUMENTS

| | | |
|---|---|---|
| 0486425 | 5/1992 | European Pat. Off. |
| 0210024 | 11/1984 | Japan. |
| 1118608 | 1/1968 | United Kingdom. |
| 2196523 | 5/1988 | United Kingdom. |

| | | |
|---|---|---|
| 91/19692 | 12/1991 | WIPO. |
| 92/19251 | 11/1992 | WIPO. |
| 92/21355 | 12/1992 | WIPO. |
| 95/05808 | 3/1995 | WIPO. |

OTHER PUBLICATIONS

Woodroof et al., Beverages: Carbonated and Noncarbonated, AVI Publishing, 1974, pp. 143–146.
Melillo, Food Products Development, Jun. 1977, pp. 108–110.
Data From the National Health Survey, Series II, No. 231, DHHS Pub. No. (PHS) 83–1681, p. 20 (1983).
Melillo Physical Factors Governing the Stabilization of Cloudy Beverages, Jun., 1977, *Food Product Development*, pp. 108 to 110.
Kelly et al., Gastroenterology, 87: 596–600 (1984).
Bei et al., American Journal of Clinical Nutrition, 44:244–247 (1986).
Beuchat, Food and Beverage Mycology, Van Nostrand Reinhold, 1987, pp. 120–122.
Smith et al., Calcified Tissue International, 41:351–352 (1987).
Nationwide Food Consumption Survey, USDA NFCS, Report 86–3, (1988), pp. 62 and 75.
Spencer et al., Journal of Nutrition, 118:657–660, (1988).
Champagne, Advances in Experimental Medicine and Biology, 249:173–184 (1989).
Mehansho et al., Journal of the American College of Nutrition, 8(1):61–68 (1989).
Churella et al., The FASEB Journal, 4(3):A788 (1990).
Hanning et al., American Journal of Clinical Nutrition, 54:903–908 (1991).

(List continued on next page.)

*Primary Examiner*—Melvyn I. Marquis
*Assistant Examiner*—Robert H. Harrison
*Attorney, Agent, or Firm*—Donald O. Nickey; Thomas D. Brainard; Lonnie R. Drayer

[57] ABSTRACT

A calcium supplement in solid form contains calcium glycerophosphate, vitamin D and vitamin C.

7 Claims, 11 Drawing Sheets

OTHER PUBLICATIONS

Draper et al., Journal of Parenteral and Enteral Nutrition, 15(2):176–180 (1991).
Sakhee et al., Bone and Mineral, 20:87–97 (1993).
Wardlaw, Journal of the American Dietetic Association, 93(9):1000–1006 (1993).
Journal of the American Medical Association, 272(24):1942–1948 (1994).
Whiting, Nutrition Reviews, 52(3):95–97 (1994).
56 FR 60689–60726 (1991).
Label for Tums 500 ™.
Label for Sunny Delight® with Calcium.
Label for Hawaiian Punch® Double C.
Federal Register, 58(3):2665–2681 (1993).
Physicians Desk Reference, 19th Edition, Published 1965, p. 1015.
Physicians Desk Reference, 48th Edition, Published 1994, p. 1155.

CALCIUM SUPPLEMENT

FIELD OF THE INVENTION

The present invention relates to a solid calcium supplement which is fortified with calcium glycerophosphate, vitamin D and vitamin C.

BACKGROUND OF THE INVENTION

Calcium is an essential nutrient; it is a major component of mineralized tissues and is required for normal growth and development of the skeleton and teeth. Over the last decade calcium has enjoyed increased attention due to its potential role in the prevention of osteoporosis. Osteoporosis affects more than 25 million people in the United States and is the major underlying cause of bone fractures in postmenopausal women and the elderly. "Optimal Calcium Intake", JOURNAL OF THE AMERICAN MEDICAL ASSOCIATION, 272(24): 1942–1948 (1994).

As used herein "osteoporosis" refers to a reduction in the amount of bone mass. Two important factors influencing the occurrence of osteoporosis are optimal peak bone mass attained in the first two to three decades of life and the rate at which bone mass is lost in later years. Adequate calcium intake is critical to achieving optimal peak bone mass and modifies the rate of bone mass loss associated with aging. Wardlaw, "Putting osteoporosis in perspective", JOURNAL OF THE AMERICAN DIETETIC ASSOCIATION, 93(9): 1000–1006 (1993).

Several cofactors modify calcium balance and influence bone mass. These include dietary constituents, hormones, drugs, and the level of physical activity. Unique host characteristics may also modify the effects of dietary calcium on bone health. These include the individual's age and ethnic and genetic background, the presence of gastrointestinal disorders such as malabsorption and the postgastrectomy syndrome, and the presence of liver and renal disease. Interactions among these diverse cofactors may affect calcium balance in either a positive or negative manner and thus alter the optimal levels of calcium intake. "Optimal Calcium Intake", JOURNAL OF THE AMERICAN MEDICAL ASSOCIATION, 272(24): 1942–1948 (1994).

Calcium requirements vary throughout an individual's lifetime with greater needs occurring during the period of rapid growth in childhood and adolescence, pregnancy and lactation, and in later adult life. Table 1 presents the optimal calcium requirements which were established at a National Institute of Health (NIH) conference on optimal calcium intake held Jun. 6–8, 1994. "Optimal Calcium Intake", JOURNAL OF THE AMERICAN MEDICAL ASSOCIATION, 272(24): 1942–1948, at 1943 (1994). The participants at the NIH conference considered former Recommended Dietary Allowances (RDA) (10th edition, 1989) for calcium intake as reference levels and used them as guidelines to determine optimal calcium intake in light of new data on calcium-related disorders.

TABLE 1

OPTIMAL CALCIUM INTAKES

| GROUP | OPTIMAL DAILY INTAKE (in mg of calcium) |
|---|---|
| Infants | |
| Birth–6 months | 400 |
| 6 months–1 year | 600 |
| Children | |
| 1–5 years | 800 |
| 6–10 years | 800–1,200 |
| Adolescents/Young Adults | |
| 11–24 years | 1,200–1,500 |
| Men | |
| 25–65 years | 1,000 |
| Over 65 years | 1,500 |
| Women | |
| 25–50 years | 1,000 |
| Over 50 years (postmenopausal) | |
| On estrogens | 1,000 |
| Not on estrogens | 1,500 |
| Over 65 | 1,500 |
| Pregnant and nursing | 1,200–1,500 |

National consumption data indicate most females over the age of eleven, as well as elderly men, consume amounts of calcium below recommended levels. "Nationwide Food Consumption Survey, Continuing Survey of Food Intakes of Individuals", USDA NFCS, CFS II Report No. 86–93 (1988), pages 62 and 75. According to the Second National Health and Nutrition Examination Survey, the median daily calcium intake for women in the United States was 574 mg. DIETARY INTAKE SOURCE DATA: UNITED STATES, 1976–80, Data From the National Health Survey, Series II, No. 231, DHHS Publication No. (PHS), 83–1681 (1983) page 20.

The preferred approach to attaining optimal calcium intake is through dietary sources. Dairy products are the major contributors of dietary calcium because of their high calcium content (e.g. approximately 250–300 mg/8 oz of cow's milk) and frequency of consumption. As used herein the term "milk" is understood to refer to cow's milk, and the term "dairy products" is understood to refer to food products derived from cow's milk. However, many persons, especially women, prefer to limit their intake of dairy products for several reasons: (a) they dislike the taste of milk/milk products; and/or (b) they have a lactose intolerance; and/or (c) they perceive that some dairy products are too high in fat or protein and may lead to weight gain. Other good food sources of calcium include some green vegetables (e.g. broccoli, kale, turnip greens, Chinese cabbage), calcium-set tofu, some legumes, canned fish, seeds and nuts. Breads and cereals, while relatively low in calcium, contribute significantly to calcium intake because of their frequency of consumption. A number of calcium-fortified food products are currently available, including fortified juices, fruit drinks, breads and cereals. Consumption of these foods may be an additional strategy by persons to achieve their optimal calcium intake.

To maximize calcium absorption, food selection decisions should include consideration of information on the bioavailability of the calcium contained in the food. Bioavailability (absorption) of calcium from food depends on the food's total calcium content and the presence of components which enhance or inhibit calcium absorption. Bioavailability of minerals in food has been traditionally tested by the balance method, which estimates absorption from the difference between ingested intake and fecal output. This approach works well for many nutrients where the difference between intake and excretion is large, but is less well suited for an element such as calcium entering the digestive tract with its secretions. A decline in fractional absorption from 30% to 20% could have profound nutritional significance but would be difficult to detect using the balance method. In contrast, isotopic methods estimate absorption directly from the appearance of the ingested tracer in body fluids. Future clinical evaluations of the bioavailability of calcium from the liquid nutritional product of the present invention will use a state-of-the-art isotope tracer method.

Not all calcium salts are created equally. Calcium salts range from 9% elemental calcium in calcium gluconate to 40% calcium in calcium carbonate. Bioavailability depends on solubility. A new calcium delivery system, Calcium Citrate Malate (CCM) claims to be approximately six-times the solubility of either calcium citrate or calcium malate, both of which are themselves substantially more soluble than calcium carbonate. Smith et al., "Calcium Absorption from a New Calcium Delivery System (CCM)" CALCIFIED TISSUE INTERNATIONAL, 41: 351–352 (1987) relates an experiment in humans wherein calcium from CCM was absorbed significantly better than from either calcium carbonate or milk. 38.3% vs 29.6% and 29.4% respectively. WO 91/19692 discloses a process for making a metastable calcium citrate malate.

However, the United States Food and Drug Administration (FDA) has advised that, in order for calcium-containing food ingredients in conventional foods or calcium supplement products to be considered eligible to bear the authorized calcium/osteoporosis health claim, they must meet the requirements in §101.14, which include that they have been shown to the FDA's satisfaction to be safe and lawful under the applicable safety provisions of the act (56 FR at 60699). Safety and lawfulness can be demonstrated in a number of ways, including through a showing that a food is generally recognized as a safe (GRAS), affirmed as GRAS by the FDA, listed in the food additive regulations, or subject to a prior sanction. Of the 36 or more calcium-containing ingredients identified by the agency as currently in use the FDA advised that only the following 10 compounds had been demonstrated to be safe and lawful for use in a dietary supplement or as a nutrient supplement: calcium carbonate, calcium citrate, calcium glycerophosphate, calcium oxide, calcium pantothenate, calcium phosphate, calcium pyrophosphate, calcium chloride, calcium lactate, and calcium sulfate (56 FR at 60691).

Table 2 summarizes the enhancement and inhibition factors associated with calcium absorption.

TABLE 2

FACTORS WHICH ENHANCE OR INHIBIT CALCIUM ABSORPTION

| Inhibitors | Enhancers |
|---|---|
| Older age (>51) | Younger age (11–24) |
| Vitamin D deficiency | Healthy vitamin D levels |
| Oxalic acid, fiber & phytates (only if achlorhydria present) | Pregnancy & lactation |
| | Estrogen (natural & replacement therapy) |
| Caffeine | Adequate protein intake |
| Presence of other nutrients in $Ca^{+2}$ supplement | $Ca^{+2}:PO_4$ ratio of 1:1 |

TABLE 2-continued

FACTORS WHICH ENHANCE OR INHIBIT CALCIUM ABSORPTION

| Inhibitors | Enhancers |
|---|---|
| Excess protein intake > 2 × RDA | Specific disaccharides: fructose & lactose |
| | Specific organic acids: |
| | Citric |
| | Malic |
| | Ascorbic |

Calcium absorption is directly affected by an individual's vitamin D status. Vitamin D deficient individuals absorb less calcium than individuals whose vitamin D stores are adequate. Vitamin D metabolites enhance calcium absorption. The major metabolite 1,25-dihydroxyvitamin D, stimulates active transport of calcium in the small intestine and colon. Deficiency of 1,25-dihydroxyvitamin D, caused by inadequate dietary vitamin D, inadequate exposure to sunlight, impaired activation of vitamin D, or acquired resistance to vitamin D, results in reduced calcium absorption. In the absence of 1,25-dihydroxyvitamin D, less than 10 percent of dietary calcium may be absorbed. Vitamin D deficiency is associated with an increased risk of fractures. Elderly patients are at particular risk for vitamin D deficiency because of insufficient vitamin D intake from their diet, impaired renal synthesis of 1,25-dihydroxyvitamin D, and inadequate sunlight exposure, which is normally the major stimulus for endogenous vitamin D synthesis. This is especially evident in homebound or institutionalized individuals. Supplementation of vitamin D intake to provide 600–800 IU/day has been shown to improve calcium balance and reduce fracture risk in these individuals. Sufficient vitamin D intake should be ensured for all individuals, especially the elderly who are at greater risk for development of a deficiency. Sources of vitamin D, besides supplements include sunlight, vitamin D-fortified liquid dairy products, cod liver oil, and fatty fish. Calcium and vitamin D need not be taken together to be effective. Excessive doses of vitamin D may introduce risks such as hypercalciuria and hypercalcemia and should be avoided. Anticonvulsant medications may alter both vitamin D and bone mineral metabolism particularly in certain disorders, in the institutionalized, and in the elderly. Although symptomatic skeletal disease is uncommon in noninstitutionalized settings, optimal calcium intake is advised for persons using anticonvulsants. "Optimal Calcium Intake", JOURNAL OF THE AMERICAN MEDICAL ASSOCIATION, 272(24): 1942–1948 (1994). A number of other dietary factors can also affect calcium absorption. Dietary fiber and phytate have been implicated as inhibiting substances. The binding of calcium by dietary fiber increases with increasing pH. The onset of precipitation of calcium phytates occurs in the pH 4–6 range as in achlorhydria. At low gastric pH values (2–3), phytate does not bind calcium and calcium binding by dietary fiber would be weak if at all. Thus, in normal individuals calcium would reach intestinal sites as soluble species. Depending on the concentrations and binding strengths of various food ligands, some of the calcium will be absorbed at the intestinal sites while the remainder becomes bound as insoluble fiber and phytate complexes. Champagne, "Low Gastric Hydrochloric Acid Secretion and Mineral Bioavailability", ADVANCES IN EXPERIMENTAL MEDICINE AND BIOLOGY, 249: 173–184 (1989).

Simple sugars and organic acids also have an effect on bioavailability. Fructose in orange juice and apple juice promoted positive calcium bioavailability from Calcium Citrate Malate (CCM) which is a combination of $CaCO_3$, citric acid, malic acid: 5:1:1 mol/mol/mol). The lactose in milk forms a soluble compound with calcium. Organic acids such as citric acid, malic acid and ascorbic acid may also play a role in the favorable absorption of calcium from CCM. Mehansho et al., "Calcium Bioavailability and Iron-Calcium Interaction in Orange Juice", JOURNAL OF THE AMERICAN COLLEGE OF NUTRITION, 8(1): 61–68 (1989).

In addition, it is known that high protein intakes, specifically of sulfur containing amino acids, increase urinary calcium excretion. Sulfuric acid radicals are believed to decrease renal tubular resorption. However, consumption of high phosphorus foods, such as meat, can diminish this effect. Spencer et al., "Do Protein and Phosphorous Cause Calcium Loss?", JOURNAL OF NUTRITION, 118: 657–660 (1988).

For some individuals, calcium supplements may be the preferred way to obtain optimal calcium intake. Although calcium supplements are available in many salts, calcium carbonate is usually recommended because it contains more elemental calcium per gram than any of the other salts. The disintegration and dissolution characteristics of commercial calcium carbonate preparations, which vary widely, may produce important differences in calcium absorption. Other problems with using large amounts of calcium carbonate is that it can lead to constipation and abdominal distention. When problems arise, calcium lactate or calcium citrate are advised. These substitutions for calcium carbonate are also indicated for people with achlorhydria. A popular commercially available calcium supplement is TUMS 500™ which is distributed by SmithKline Beecham, Pittsburgh, Pa., U.S.A. and is labeled as providing 500 mg of elemental calcium (from calcium carbonate per. tablet). However, the TUMS 500™ label does not indicate that this calcium supplement contains any vitamin D.

U.S. Pat. No. 4,786,510 and U.S. Pat. No. 4,992,282 disclose the use of calcium citrate malate in a beverage or dietary supplement fortified with iron, but do not disclose the addition of vitamin D to such a product. WO 92/19251 and WO 92/21355 disclose the use of calcium citrate malate in a low pH beverage, and suggests that vitamin D be added to such a beverage along with oil flavors or weighing oil. However; neither WO 92/19251 or WO 92–21355 disclose any other details about how to incorporate vitamin $D_3$ into such a beverage.

EP 0 486 425 A2 discloses a liquid oral nutritional formulation which contains carbohydrates, protein, fat, fiber, calcium, and vitamin D, and has a pH of about 3.5 to 3.9. However, this publication teaches that high amounts of micronutrients such as calcium or magnesium may impair the palatability of the product, and should contain the recommended daily allowance of these nutrients in about one liter or product. In an example in the patent publication this product contains only about 570 mg of calcium per liter and about 211 IU of vitamin D per liter. A commercially available product in accordance with this patent publication is distributed by Sandoz Nutrition under the trade name CITRISOURCE® and is labeled as providing 570 mg of calcium and 210 IU of vitamin D per liter. By way of comparison, prototypes of a beverage according to the present invention contain about 1,408 mg of calcium per liter and about 338 IU of vitamin $D_3$ per liter.

U.S. Pat. No. 4,737,375 teaches beverage concentrates and beverages having a pH of 2.5 to 6.5, preferably 3.0 to 4.5, which contains calcium. The use of vitamin $D_3$ in this beverage is not disclosed. This patent does not teach the use of calcium glycerophosphate (which is used in preferred embodiments of the present invention, as a calcium source. The acidulants used in this prior art beverage are chosen from mixtures of citric acid, malic acid and phosphoric acid, and the weight ratio of total acids to calcium is in the range of 4 to 7. The calcium level is 0.06% to 0.15%, preferably 0.10% to 0.15% of the beverage, by weight. By way of comparison, prototypes of the beverage of the present invention have a weight ratio of total acids to calcium of about 5.1.

Two commercially available beverages which are labeled as being protected by U.S. Pat. No. 7,737,375 are: (1) Sunny Delight® With Calcium which is distributed by Procter & Gamble, Cincinnati, Ohio 45202 U.S.A.; and (2) HAWAIIAN PUNCH®, DOUBLE C which is distributed by Sundor Brands, Inc., Cincinnati, Ohio 45202 U.S.A.. According to the "Nutrition Facts" on the labels of these commercially available products: (a) either product contains vitamin D; (b) neither product contains any fat; (c) a 240 mL (8 fluid ounce) serving of Sunny Delight® With Calcium provides 30% of the recommended daily intake of calcium; (d) a 240 mL (8 fluid ounce) serving of HAWAIIAN PUNCH®, DOUBLE C provides 15% of the recommended daily intake of calcium; and (e) and a 240 mL (8 fluid ounce) serving of each of these products provides 100% of the recommended daily intake of vitamin C. Per the product labels, these percent daily values are based on a 2,000 calorie diet. A review of the ingredient listings on the labels of each of these products indicates that both of these beverages are aqueous solutions, and that neither product contains gum arabic. Samples of each of these products were tested regarding their pH values: the pH value of the HAWAIIAN PUNCH® DOUBLE C was 3.91; and the pH value of the Sunny Delight® With Calcium was 4.05.

GB 2 196 523 A discloses a beverage containing calcium and vitamin D. A water soluble non-toxic calcium salt is used in a quantity sufficient to provide in the final beverage a calcium ion content of from $1.0 \times 10^{-2}$ to $40 \times 10^{-2}$% w/w. The beverage may contain up to $5 \times 10^{-6}$ w/w of vitamin D. However, this published patent application does not teach the use of a gum, such as gum arabic or gum tragacanth, in such a beverage to improve vitamin $D_3$ stability.

The NIH Consensus Statement recommended that the private sector play an active role in promoting optimal calcium intake by developing and marketing a wide variety of calcium-rich foods to meet the needs and tastes of a multiethnic population. "Optimal Calcium Intake", JOURNAL OF THE AMERICAN MEDICAL ASSOCIATION, 272 (24): 1942–1948 (1994). Hence, there is provided in accordance with one aspect of the present invention a low pH beverage fortified with calcium and vitamin $D_3$. There is provided in accordance with another aspect of the invention a liquid beverage concentrate fortified with calcium and vitamin $D_3$. There is provided in accordance with yet another aspect of the invention a liquid beverage additive fortified with calcium and vitamin $D_3$.

DETAILED DESCRIPTION OF THE INVENTION

Figure 1:
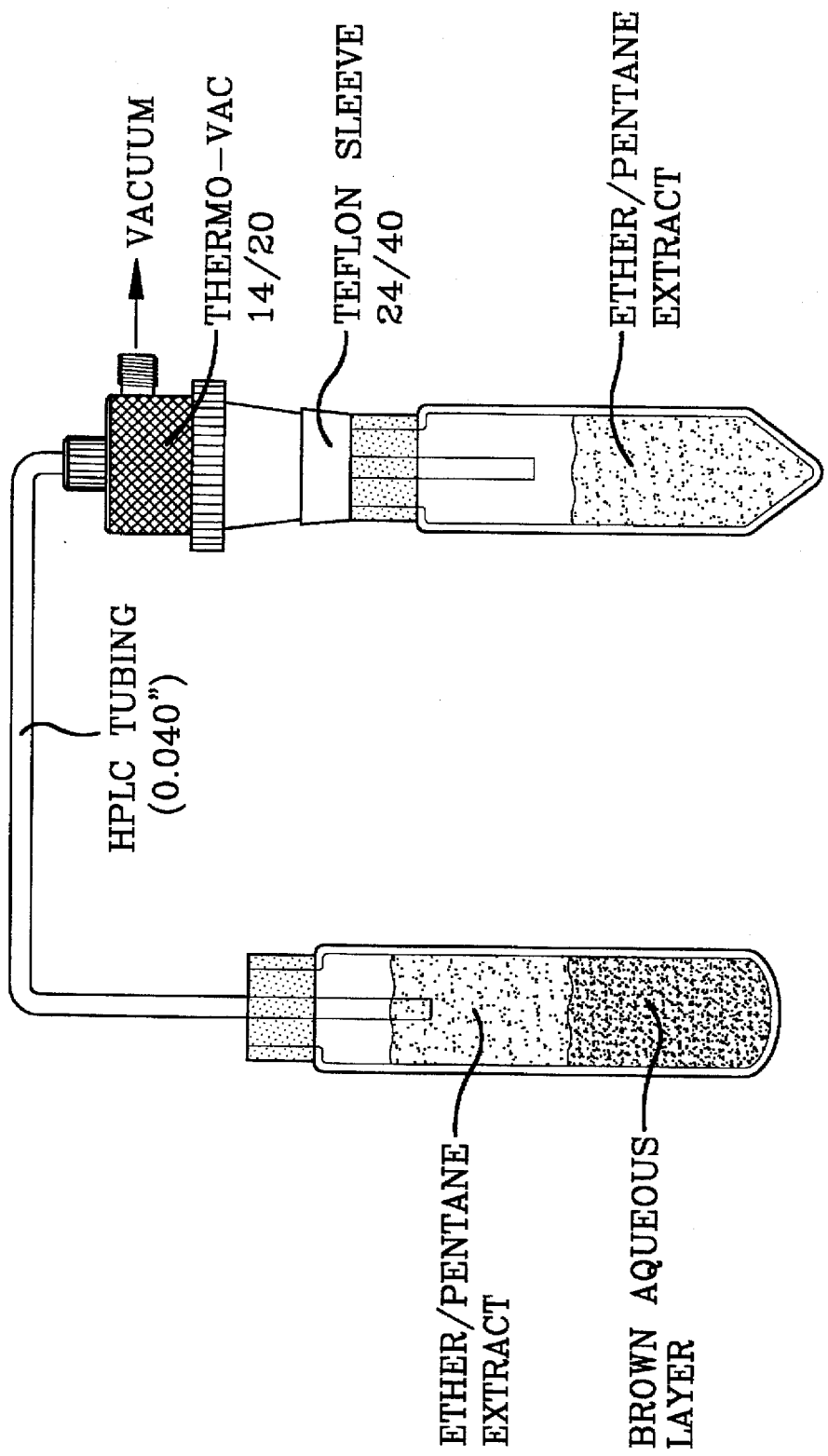
FIGS. 1–7 are representative of the methodology used in determining vitamin $D_3$ levels.
Figure 2:
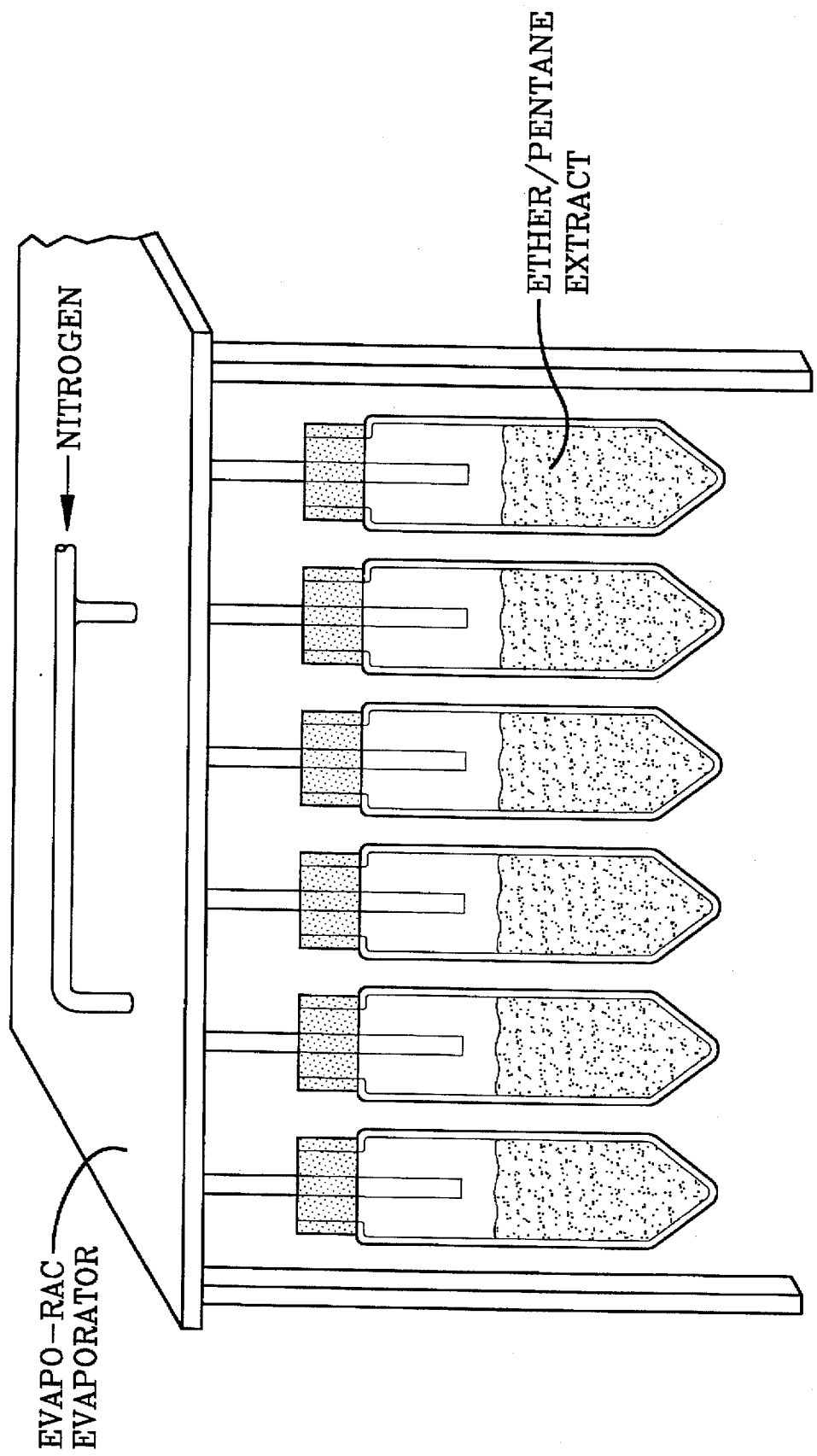
Figure 3:
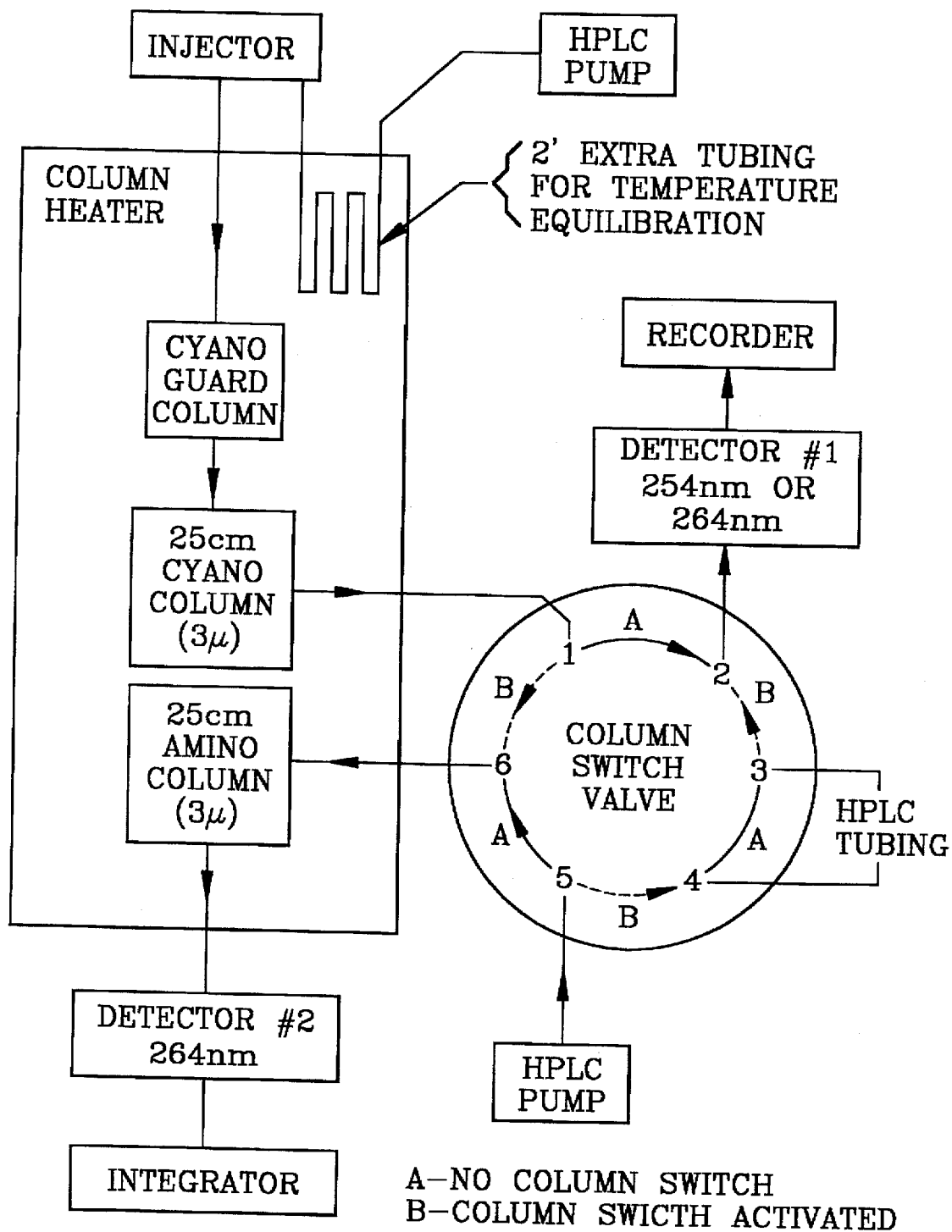

The levels, half lives and other characteristics and properties of vitamin $D_3$, calcium and vitamin C referred to herein and in the claims were determined, and in the interpretation of the claims are to be determined, according to the following methods.

VITAMIN $D_3$ ASSAY

Refer to FIGS. 1–7 regarding the performance of this vitamin $D_3$ assay.

I. OVERVIEW OF THE METHOD

The low pH beverage, the vitamin $D_3$ emulsion and the powder beverage are saponified with methanolic potassium hydroxide to destroy the fat and release the vitamin $D_3$ for extraction. The saponified samples are extracted with an ether/pentane mixture and the extracts are evaporated to dryness using nitrogen and reconstituted with iso-octane. Sample extracts are eluted on a cleanup HPLC column (cyanopropyl bonded silica), and column switching is used to transfer a "slice" of the eluant containing vitamin $D_3$ onto an additional HPLC analytical column (aminopropyl bonded silica) for final quantitation. The vitamin $D_3$ peak in the sample is quantitated using a linear regression external standard curve.

II. APPARATUS

A. General Apparatus
1. Centrifuge tube glass, 50 ml with teflon-lined screw cap (Corex 8422A).
2. Centrifuge tube glass, 50 ml—conical (Kimax 45176).
3. Centrifuge (IEC Model Centra-HN or equivalent).
4. Water bath -capable of 40($\pm$2)° C. and 75($\pm$2)° C.
5. Source of nitrogen (purity >99.7%)—for evaporations.
6. Vortex mixer—SIP Magnestir or equivalent.
7. Volumetric flasks—100 ml, 500 ml.
8. Volumetric pipets—1 ml, 2 ml, 3 ml, 5 ml, 7 ml, 15 ml, 30 ml.
9. Repeating pipet—"Tilt-a-Pet"2–25 ml heads (VWR—53481-406) for ether/pentane 2–1000 ml Erlenmeyer flask reservoirs—size 24/40.
10. Repipet Dispensers—Baxter-P4985 or equivalent
    1 ml for KCL solution (Baxter P4985-5)
    5 ml for acetonitrile (Baxter P4985-10)
    6 ml for methanol (Baxter P4985-10).
11. Oxford Macro-Set Pipetter (Baxter—P5079-2, or equiv; Qty =2)
    1 —for sample transfer
    1–4 ml for 45% KOH.
12. Therm-O-Vac—size 14/20 (Cole-Parmer #N-06140-15).
13. Teflon sleeves—sizes 24/40 (Cole-Parmer #N-06139-15).
14. Evapo-Rac Evaporator for 30 mm tubes (Cole-Parmer #N-01610-35).
15. Centrifuge tube rack (Cole-Parmer #N-06737-40).
16. Cooling tray large enough to accommodate centrifuge tube rack (#N 06737-40).
17. HPLC tubing—0.040" stainless steel—2 feet.
18. Balances—
    (a) Merrier AT200 (or equivalent) readable to at least 0.01 mg (for standards, vitamin $D_3$ emulsion and powdered product.
    (b) Mettler PM460 (or equivalent) readable to at least 0.001 g (for low pH beverage samples).
19. Glass Stirring Rods.
20. Magnestir Stir Plate—Lab Line #1250 or equivalent.
21. Teflon Coated Stir Bars—2" length.
22. Beakers—600 ml, 800 ml, 1000 ml.
23. Calculator—Hewlett Packard-11C or equivalent.
24. Refrigerator (freezer compartment optional) for storage of standards at 4($\pm$4)° C.
25. Lighting Requirements Ultra-violet shields—F40T12—Dayton Plastics Inc., for white fluorescent bulbs.
26. Scoop—⅛ teaspoon.

B. HPLC Instrumentation
1. Columns: Guard (4.6×30 mm)
    Cyano—Rainin—Cat. #CS-GU
    Cartridge holder—Rainin—Cat. #140-200.
    Cleanup—Chromegabond Cyano (4.6×250 mm, 3μ, 60 Angstroms) —ES Industries.
    Analytical—Hypersil APS II (4.6×250 mm, 3μ, 120 Anstroms)—Keystone.
2. Pumps: Two constant flow pumps capable of operating at 5 ml/min and up to 6000 psi (Beckman 110B with pulse dampener or equivalent).
3. Detectors: Cleanup system—fixed or variable wavelength capable of monitoring 254 nm or 264 nm( Waters 440 or equivalent).
    Analytical system—Variable wavelength detector capable of monitoring at 264 nm @0.0025 AUFS. Under normal operating conditions the short term noise should be less than 3% of the 5T vitamin $D_3$ standard peak height (Waters 486 or equivalent).
4. Injector: Alcott/Micromeritics 728, or equivalent.
5. Column Oven: Capable of 35° C.–100° C. and ±1.0° C. settings and accuracy. Storage for 2×250 mm columns and one 30 mm guard column.
6. Switching Valve: HPLC column switching valve with at least 6 ports. Has a working range up to 6000 psi (Micromeritics 732 or equivalent).
7. Recorder: One 10 mV recording device for the cleanup HPLC output and either a recorder or an integrator for the analytical HPLC system. A data system capable of monitoring, acquiring, and reprocessing two channels of data is strongly recommended.
8. Solvent Reservoir: 10 Liter—Common to both cleanup and analytical HPLC systems (VWR #KT953901-1003 or equivalent)

III. REAGENTS

A. Standard Reference Material—Vitamin $D_3$).
1. USP reference standard #1310 (Cholecalciferol= vitamin $D_3$). Consult current USP literature for the current lot number. Potency =40,000 IU per mg. Store at 2° C. to 8° C. Care must be used in opening the sealed ampules to avoid introducing glass fragments into the standard. Vitamin $D_3$ must be used from an open ampule immediately and discarded.

B. Chemicals

| | |
|---|---|
| 1. Amyl Alcohol | Analytical Reagent, recommend Mallinckrodt UN 1987. |
| 2. Methanol | HPLC Grade, recommend Burdick & Jackson #230. |
| 3. Iso-octane | HPLC Grade, recommend Burdick & Jackson #362. |
| 4. Pentane | HPLC Grade, recommend Burdick & Jackson #312. |
| 5. Diethyl Ether | Anhydrous, recommend Mallinckrodt UN 1155 |
| 6. Potassium | 45% solution, recommend Baker #3143-03. |

-continued

| | Hydroxide | |
|---|---|---|
| 7. | Sodium Ascorbate | Recommend Aldrich #26,855-0. |
| 8. | Acetonitrile | HPLC Grade, recommend Burdick & Jackson #015. |
| 9. | Chloroform | HPLC Grade, recommend Burdick & Jackson #048 |
| 10. | Potassium Chloride | Recommend Mallinckrodt #6838-500*NY. |
| 11. | n-Butyl Chloride | HPLC Grade, recommend Burdick & Jackson #034. |

C. Solutions

1. HPLC Mobile Phase Volumetrically pipet 40(±0.1) ml of n-butyl chloride, 20(±0.1) ml of amyl alcohol and 10(±0.1) ml of chloroform into 4000 ml of iso-octane. Mix well. Make four liters at a time—roughly equivalent to 1.0% n-butyl chloride +0.5% amyl alcohol+ 0.25% chloroform in iso-octane. Use for both cleanup and analytical HPLC systems. Completely fill the 10 liter reservoir prior to each day's analysis.

2. Extraction Solutions
   #1—20:80 ether/pentane: Mix 200 ml of diethyl ether with 800 ml of pentane. This is sufficient for up to 20 samples (2×25 ml per sample is required). Prepare fresh daily.
   #2—33:67 ether/pentane: Mix 250 ml of diethyl ether with 500 ml of pentane. This is sufficient for 28 samples (25 ml per sample is required). Prepare fresh daily.

3. KCL Solution
   Prepare a 10% KCL solution using distilled water. Mix 50 g of potassium chloride with distilled water and dilute to a 500 ml liter volume. Store at room temperature and expiration date is one month from date prepared if kept tightly capped.

D. Preparation of Vitamin $D_3$ Standards

NOTE: Work under UV-shielded, white, fluorescent bulbs with the ultra-violet shields described in Section II.25 if possible. If unprotected white lights are used, extra precautions must be taken to keep all solutions of Vitamin $D_3$ protected from light by covering containers with aluminum foil or by using amber low-actinic glassware. Standards are also heat sensitive and should only be briefly removed from the refrigerator for immediate use.

NOTE: Due to the method's susceptibility to low level contaminants, all volumetric flasks must be rinsed with iso-octane prior to preparation of Vitamin $D_3$ standards.

1. Stock Standard (Approximately 1,920 IU/ml) Weigh 24(±1) mg of vitamin $D_3$ into a 500 ml volumetric flask. Dissolve and bring to volume using iso-octane. Expiration date is two weeks, and it must always be stored at 2° C. to 8° C. when not being used to prepare the intermediate standard.

2. Intermediate Standard—ISTD (Approximately 27 IU/ml) Pipet 7.0 ml of stock standard into a 500 ml volumetric flask. Dilute to 500 ml with iso-octane. Expiration date is 10 hours for preparation of the working standards, but can be used for 2 months (at room temperature) for establishing the retention times on the cleanup HPLC system.

3. Working Standards—3T, 5T, 15T, 30T
   (Expiration is 1 week. Store at 2° C.–8° C.).
   3T=Pipet 3.0 ml of ISTD into a 100 ml volumetric flask and dilute to volume with iso-octane (approximately 0.8 IU/ml).
   5T=Pipet 5.0 ml of ISTD into a 100 ml volumetric flask and dilute to volume with iso-octane (approximately 1.3 IU/ml).
   15T=Pipet 15.0 ml of ISTD into a 100 ml volumetric flask and dilute to volume with iso-octane (approximately 4.0 IU/ml).
   30T=Pipet 30.0 ml of ISTD into a 100 ml volumetric flask and dilute to volume with iso-octane (approximately 8.0 IU/ml).

IV. PROCEDURE

Sample Preparation 1.a. Low pH Beverage (300 IU/KG—900 IU/KG) Accurately weigh (to the nearest 0.001 g) 12.5 g of the low pH beverage into a 50 ml centrifuge tube (Corex #8422A) and proceed to #2 in the Saponification Section.

b. Vitamin $D_3$ Emulsion (~100,00 IU/KG) Accurately weigh (to the nearest 0.0001 g) 0.1 g of the bulk emulsion into a 50 ml centrifuge tube (Corex #8422A). Add 10 ml of distilled/deionize water. Proceed to #2 in the Saponification Section.

c. Powder Product (~35,000 IU/KG) Accurately weight (to the nearest 0.0001g) 0.3 g of the powder product into a 50 ml centrifuge tube (Corex #8422A). Add 10 ml of distilled/deionize water. Proceed to #2 in the Saponification Section.

2. Add about 0.4(±0.1) g of sodium ascorbate (⅛ level teaspoon) and vortex 10 seconds. NOTE: Start with a low vortex speed and increase vortexing speed with each successive step (i.e., after the addition of methanol, and again after the addition of 45% KOH).

3. Add 6(±0.3) ml of methanol and immediately vortex for 15 seconds.

4. Add 4(±0.3) ml of 45% potassium hydroxide solution, tightly cap the tube, and immediately vortex for 20 seconds.

5. Place the tubes in a preheated water bath at 75(±2)° C. for 30 minutes. The tubes should be vortexed for 5 seconds at the 10 and 20 minute intervals.

6. After 30 minutes, remove the tubes from the water bath and place in ice water for a minimum of 30 minutes to bring them rapidly to room temperature.

Extraction

7. Add 5(±0.3) ml of acetonitrile to each tube, cap and vortex at a moderate speed for 5 seconds.

8. Add 25(±1) ml of 20% ether/80% pentane mixture and shake in a wide, semicircular arc across the front of the body 20 times. Invert the tubes with each stroke.

9. Briefly centrifuge at moderate speed (approximately 300 x G for 1 minute) to complete layer separation.

10. Draw off the clear ether/pentane using the siphoning apparatus and vacuum. (See FIG. 1). Transfer the top layer to a 50 ml conical centrifuge tube (Kimax #45176) leaving behind 4 to 8 millimeters of the ether/pentane mixture. Avoid transfer of any middle, layer or aqueous (bottom) layer. NOTE: If any of the middle or aqueous bottom layer is accidentally transferred, the sample must be discarded and the assay repeated.

11. To avoid sample to sample contamination, rinse the siphoning apparatus with 5–7 ml of pentane and add this rinse to the respective sample.

12. Evaporate the transferred ether/pentane layer in the warm water bath (40°±4° C.) with nitrogen to about 2 ml to allow for additional transfers. (See FIG. 2 for the Evapo-Rac evaporation apparatus.)

13. Repeat the extraction in steps #8–#12 once combining the extracts in the same 50 ml conical centrifuge tube. NOTE: Be careful not to overflow the 50 ml Corex centrifuge tubes with the 25 ml extraction solutions (#1 or #2) during the 2nd and 3rd extractions. Should this occur, the sample must be discarded and the assay repeated.

14. For the third extraction, follow steps #8–#12 using 25 ml of 33% ether/67% pentane solution (not the 20% ether/80% pentane solution)

15. Evaporate the combined extractions to dryness. Remove the centrifuge tubes from the water bath as soon as evaporation is complete. The extract should appear clear or as a white or slightly yellow film. Make sure that the extract is completely dried before reconstitution. The tubes may have to be gently tapped to complete the evaporation.

16. Immediately reconstitute with 2.0 (±0.006) ml of iso-octane with a class A volumetric pipet. Be careful to thoroughly rinse down the walls of the tube. The tube should be tightly capped to prevent evaporation and vortexed 5 seconds to mix.

17. Finally, add 1 ml of the KCL solution to each sample and touch to the vortexer briefly to mix. Tightly cap and centrifuge at moderate speed (approximately 300 X G) for 1 minute to complete phase separation. If using a centrifuge equipped with a swinging bucket rotor, place the centrifuge tubes on the outside perimeter of the rotor. This is to prevent the conical tubes from breaking. Transfer only the top layer to a vial and tightly cap. Be careful not to transfer any of the saturated KCL solution. NOTE: The sample extract must be analyzed within 24 hours from time of preparation. If the HPLC system encounters problems, the autosampler vial should be immediately stored below 8° C. after preparation for up to 48 hours. No sample can be reinjected after an aborted HPLC analysis if it was left in the autosampler at room temperature overnight.

18. Inject onto the equilibrated HPLC system (section V).

V. HPLC CONDITIONS

A. Cleanup HPLC System—See FIG. 3 for configuration.

| 1. Column: | Chromegabond Cyano, (4.6 × 250 mm, 3μ) with CS-GU guard column (4.6 × 30 mm). |
|---|---|
| 2. Eluant: | 1.0% 1-chlorobutane + 0.5% amyl alcohol + 0.25% chloroform in iso-octane. |
| 3. Run Time: | Slice determination = approximately 20 minutes. |
| 4. Flow Rate: | 1.5 ml/min. |
| 5. Injection Volume: | 250 μl. |
| 6. Column Heater: | 40(±1)° C. |
| 7. Detector: | 254 nm or 264 nm. |
| 8. Recorder: | Integrator or data system (preferred). |
| 9. Column Switch: | Actuated by timed control from injection point to collection. Slice time window should be no greater than 1.0 minute (with 0.1 minute accuracy) for collection of vitamin $D_3$. |

B. Analytical HPLC System—FIG. 3 for configuration.

| 1. Column: | Hypersil APS II (4.6 × 250 mm, 3μ). |
|---|---|
| 2. Eluant: | 1.0% 1-chlorobutane + 0.5% amyl alcohol + 0.25% chloroform in iso-octane. |

-continued

Figure 4:
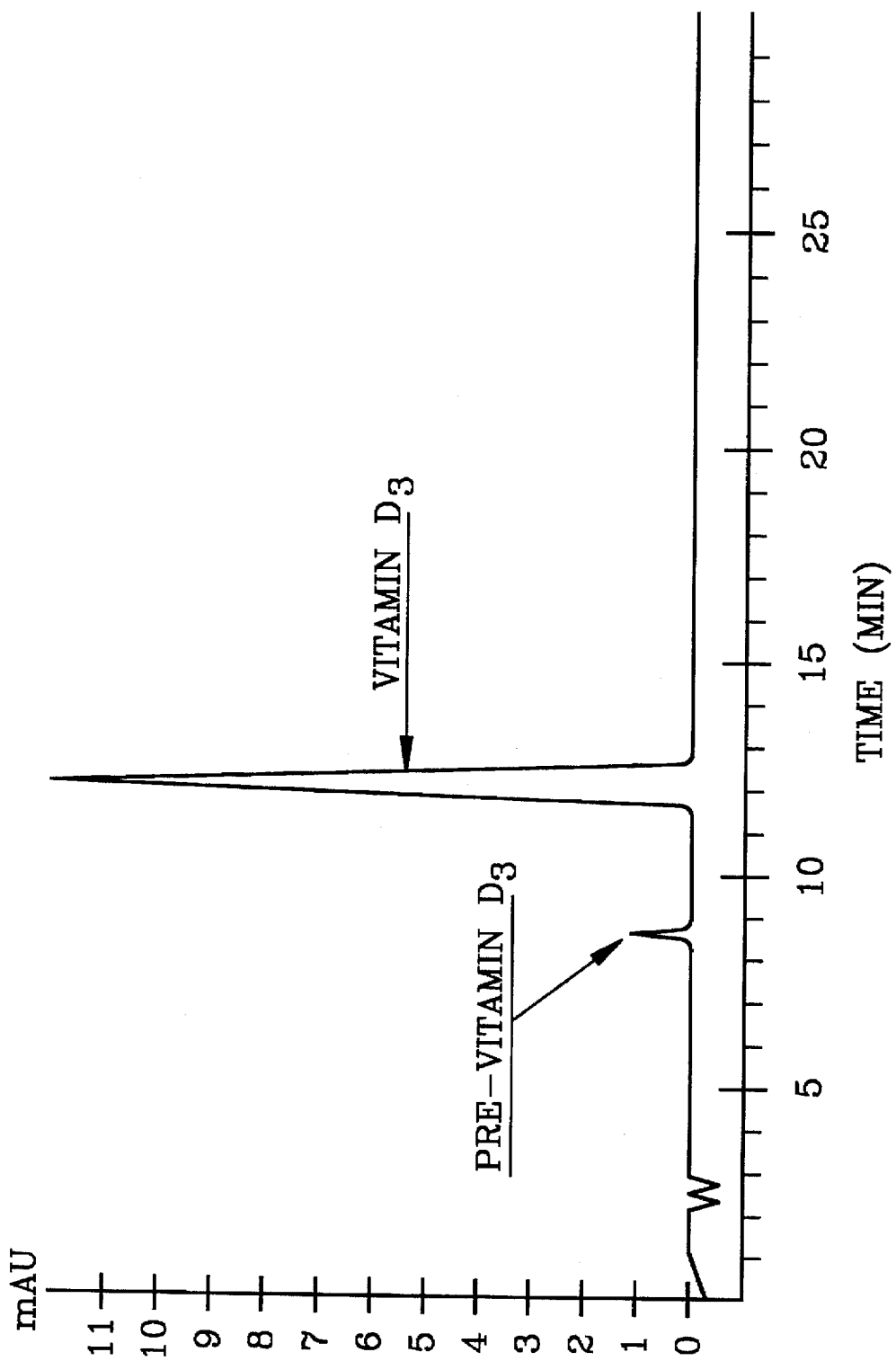
Figure 5:
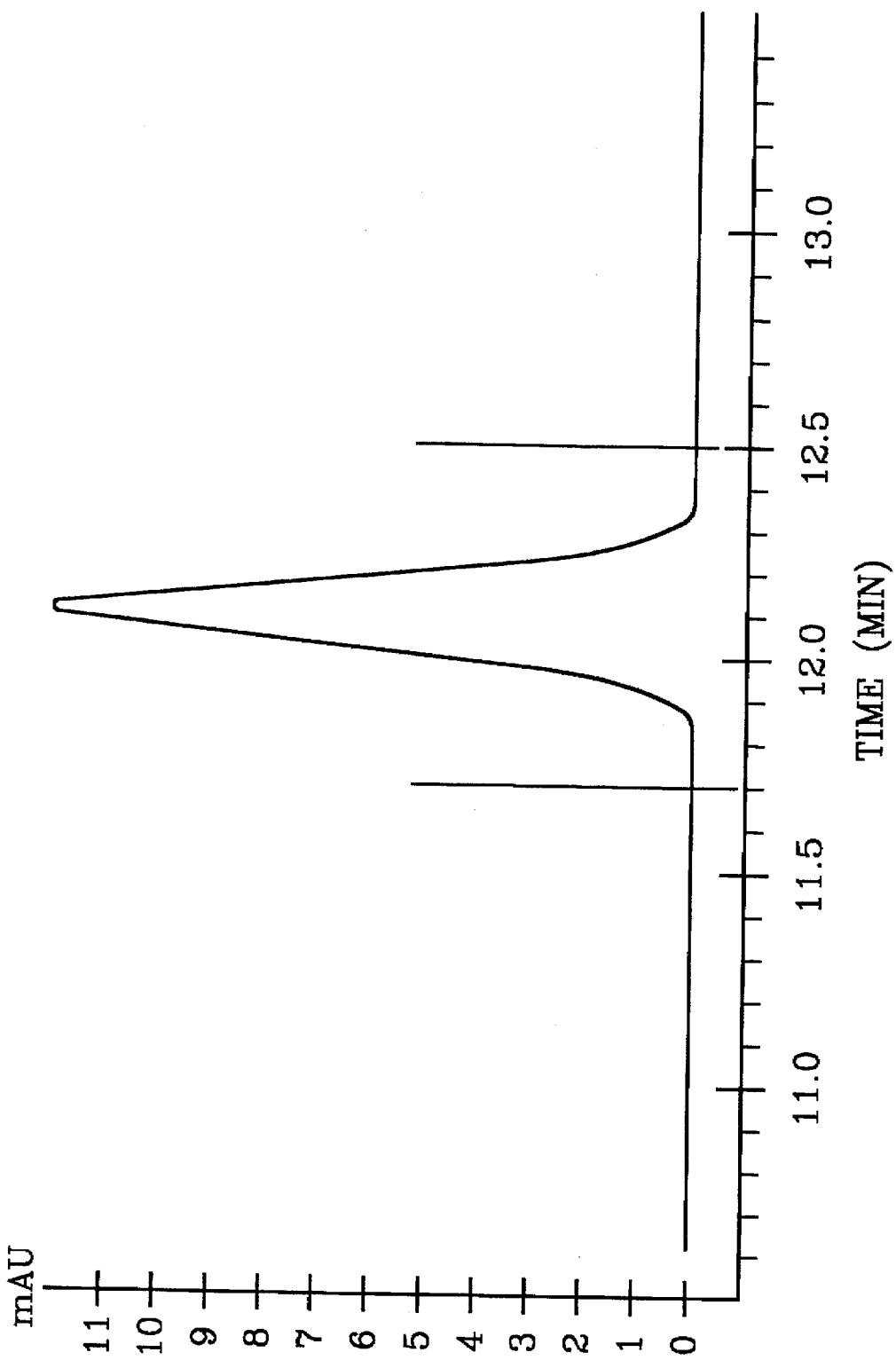
Figure 6:
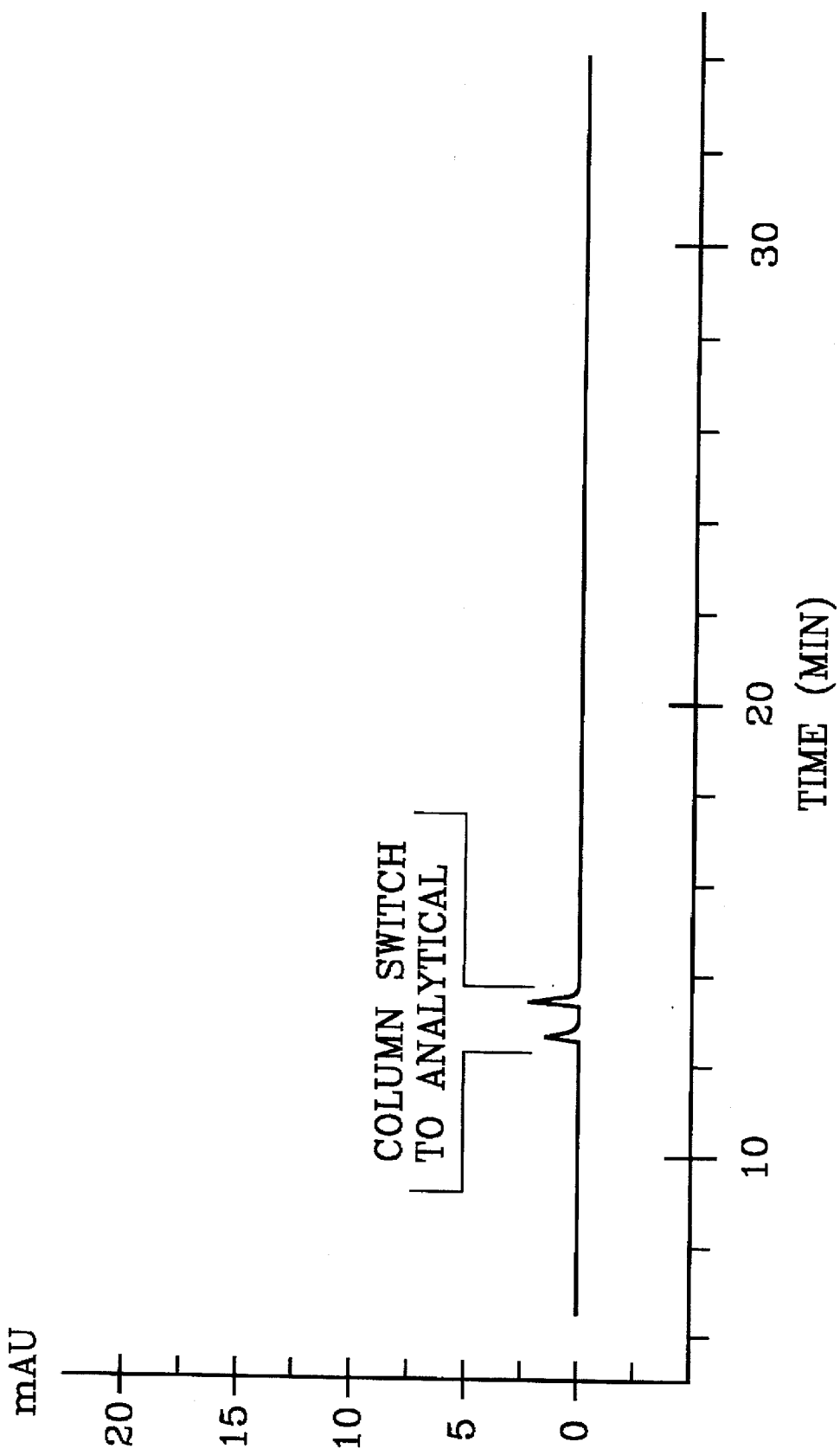
Figure 7:
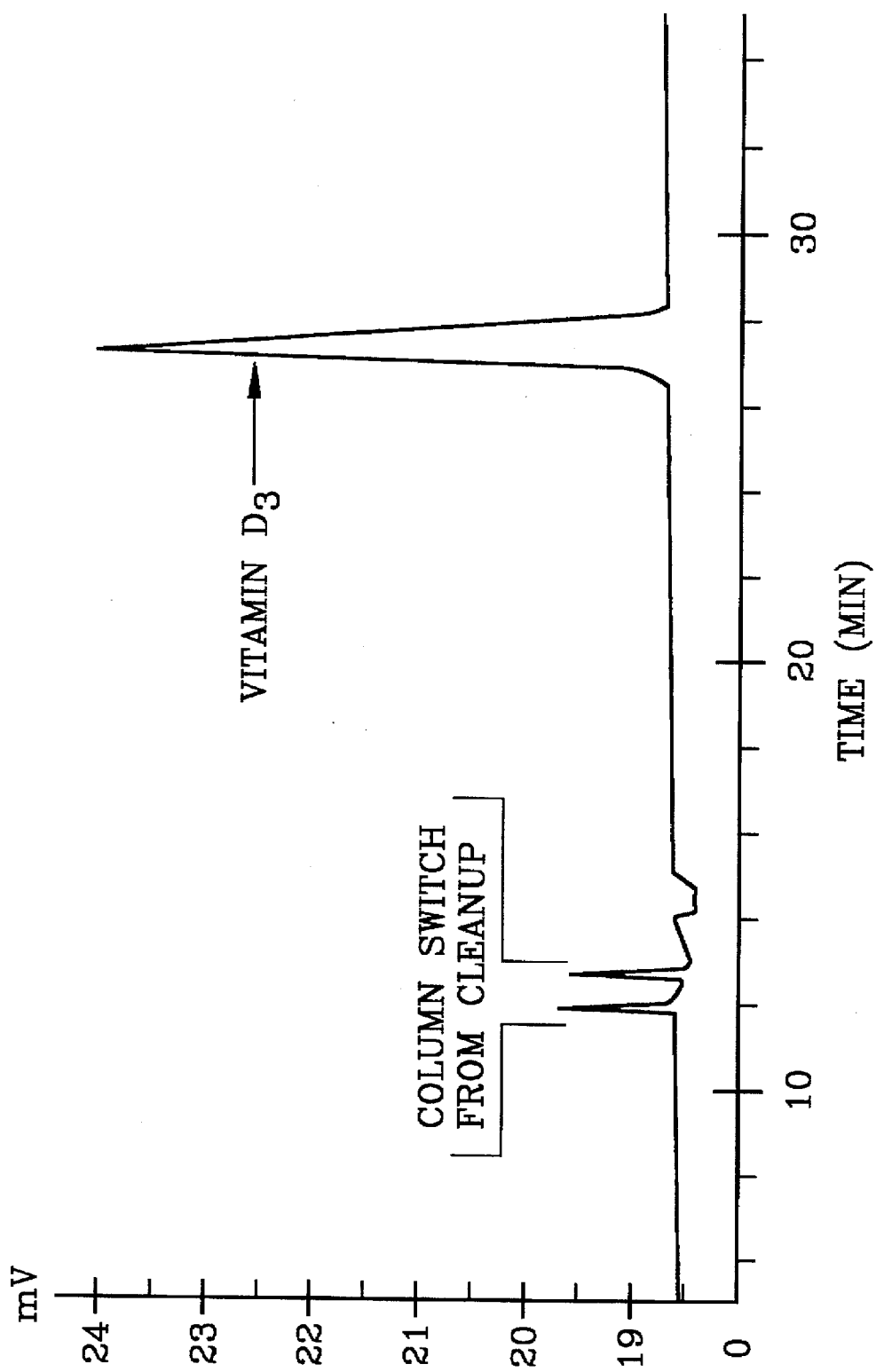
Figure 8:
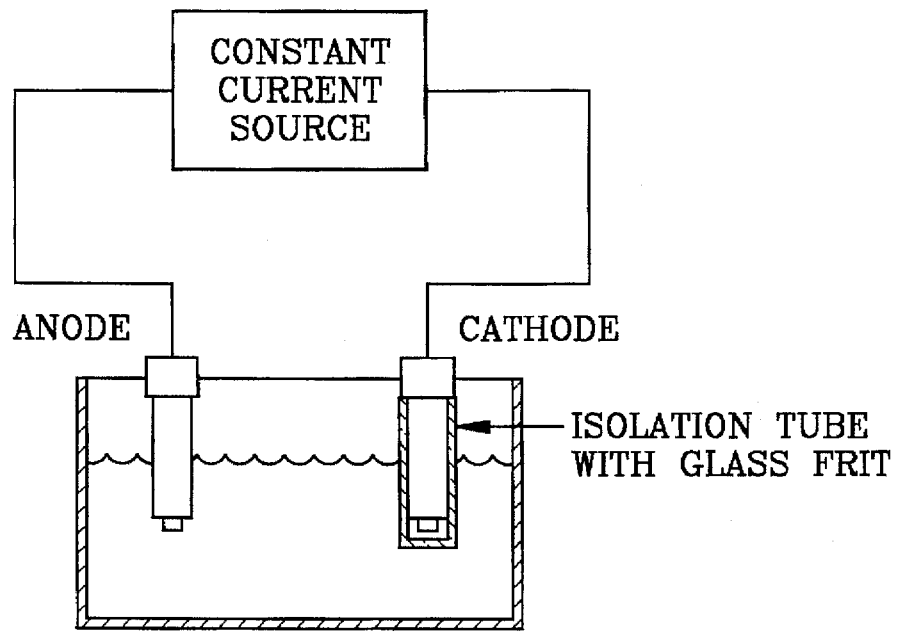
FIGS. 8–12 are representative of the methodology used in determining vitamin C levels.
Figure 9:
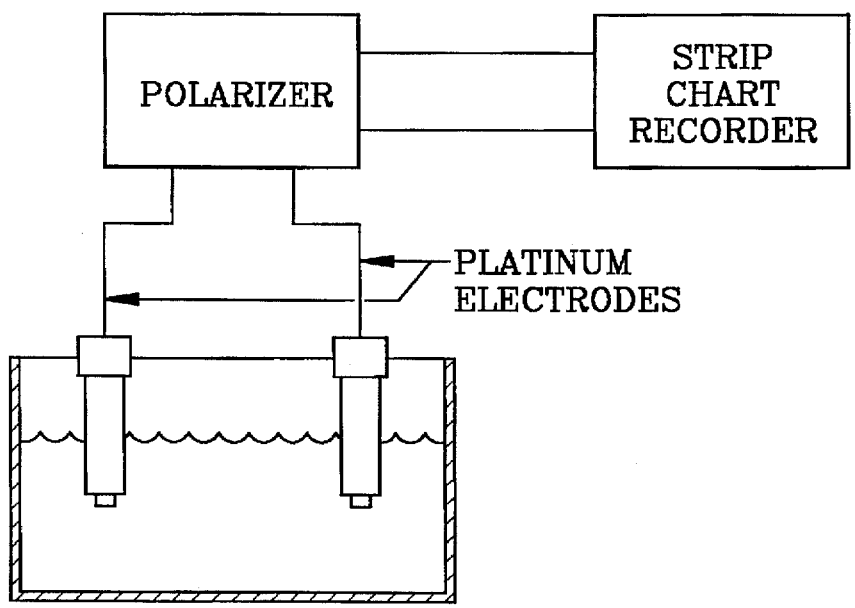
Figure 10:
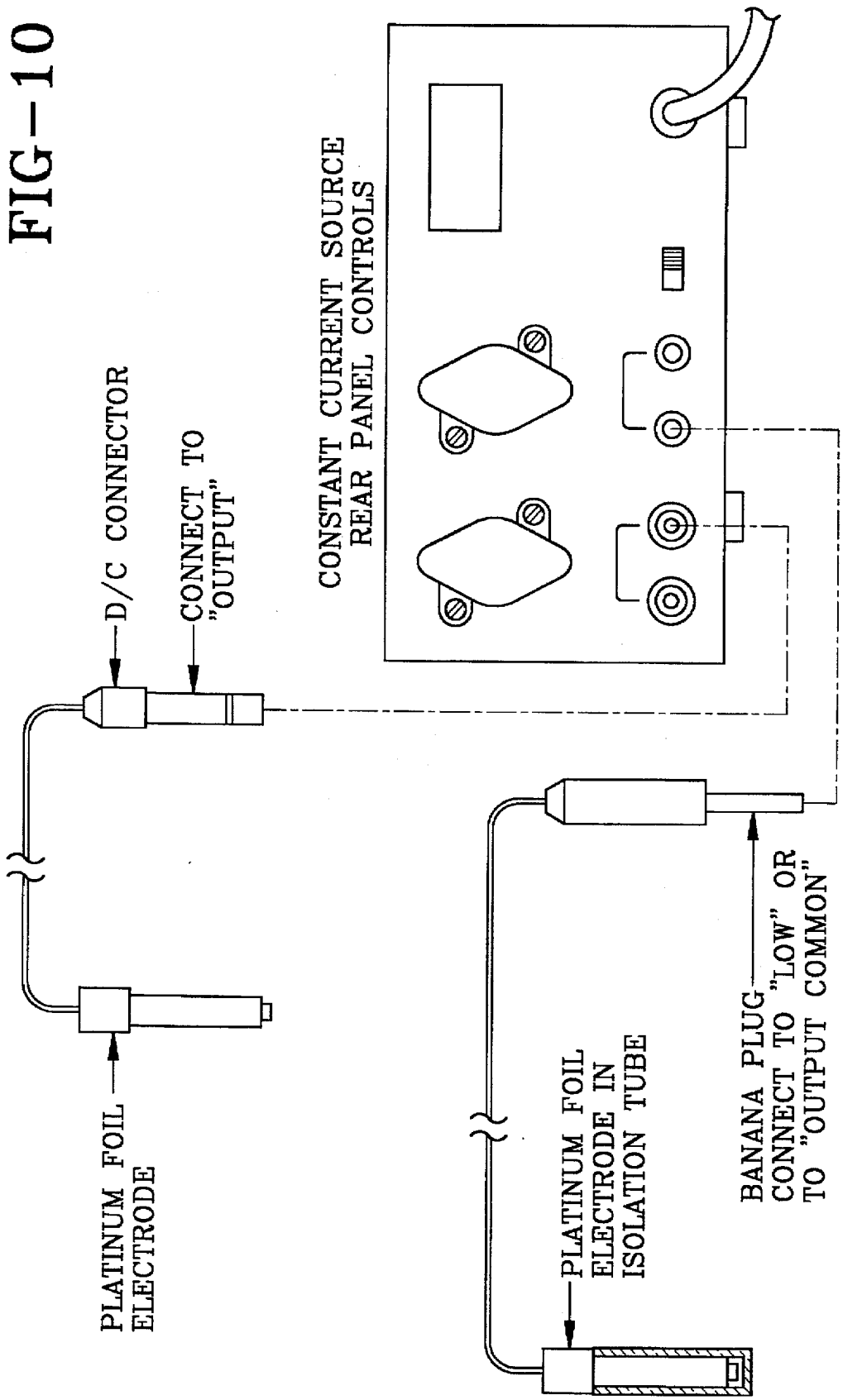
Figure 11:
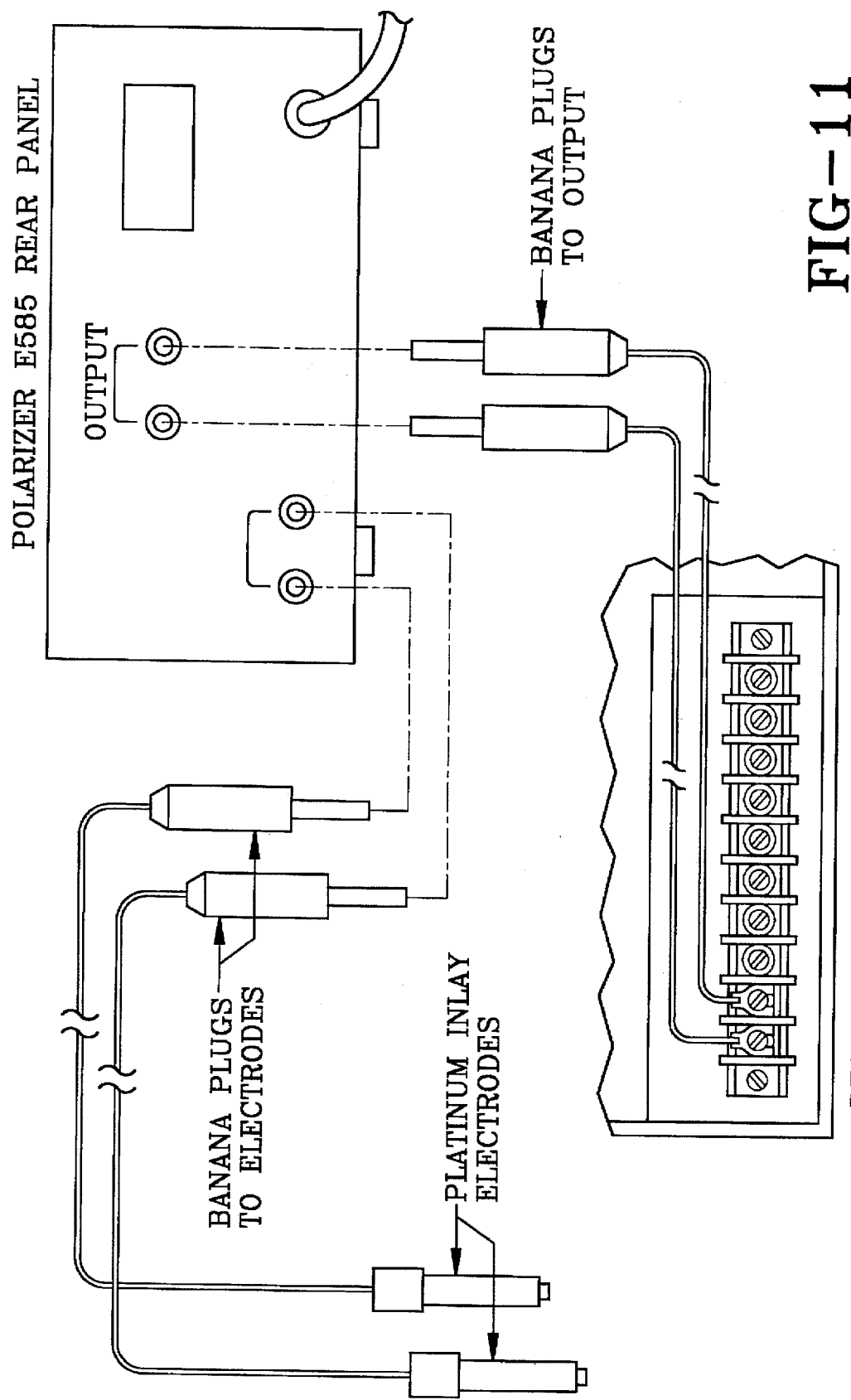

| 3. Run Time: | Approximately 35 minutes. |
|---|---|
| 4. Flow Rate: | 1.5 ml/min. |
| 5. Column Heater: | 40(±1)° C. |
| 6. Detection: | 264 nm @ 0.0025 AUFS, (Waters 486). |
| 7. Recorder: | Recommend the use of an integrator or data system for reprocessing. |
| 8. | Equilibrate the columns and obtain a stable baseline. Inject the intermediate standard ISTD (no column switch) at least 3 times until a consistent retention time (retention time ± 0.02 minutes) is established on the cleanup HPLC (FIGS. 4 & 5). Always verify the cleanup HPLC retention time within ½ hour before analysis of standards or samples. The run time is approximately 20 minutes, however the time required to equilibrate the columns with fresh eluant is approximately 2 hours. |
| 9. | After determining the retention time of the intermediate standard ISTD on the cleanup column, set the slice window (i.e. transfer of vitamin $D_3$ from the cleanup column to the analytical column). This is done by setting the switching valve to switch the vitamin $D_3$ from the cleanup column to the analytical column at 0.10 minutes before the vitamin $D_3$ first elutes from the cleanup column until 0.10 minutes after the vitamin $D_3$ peak returns to baseline on the cleanup column. See FIGS. 4 and 5. Slice window times should not exceed 1.0 minute - using a minimum among of time (generally 0.8–1.0 min.) necessary to collect all the vitamin $D_3$ while preventing the transfer of any other interfering components. See FIGS. 6 & 7 for the cleanup and analytical HPLC chromatograms of a 15T working standard. |

VI. HPLC ANALYSIS

A. Upon verifying equilibration of the HPLC system and establishing the collection window, inject three (or four) working standards (3T, 5T, 15T, 30T) and then the sample extracts. The three (or four) working standards should be injected once again at the end of the run.

Only single injections of each sample are required.

VII. CALCULATIONS (Use only peak heights for reporting purposes)

Note: Peak height is required for quantitation as small amounts of baseline noise can cause large area differences.

A. Calculation of Working Standard Concentrations

1. Calculate the concentration of the vitamin $D_3$ in working standards 3T, 5T, 15T, 30T from the following equation:

$$IU/ml = \frac{(W)(P)(7)(PV)}{(500)(500)(100)} = (W)(PV)(0.0112)$$

where: W = weight of vitamin $D_3$ standard in mg.
P = 40,000 IU/mg for vitamin $D_3$
PV = final pipet volume for working standards.
 = 3 for 3T
 = 5 for 5T
 = 15 for 15T
 = 30 for 30T.

Example: for a 5T standard prepared from a stock solution that contained 24.00 mg vitamin $D_3$, the concentration is calculated as follows:

$$IU/ml = \frac{(24.00)(40.000)(7)(5)}{(500)(500)(100)} = 1.3440 \, IU/ml$$

B. Calculation of the Standard Curve Using Linear Regression and the Quantitation of Vitamin $D_3$ in Samples 1. The peak heights of each respective level of the working standard are averaged. A linear regression line is calculated by using the average peak heights (y-axis) and the concentration (x-axis) for the respective working standard.

Example: A linear regression line (vitamin $D_3$ peak heights versus concentration) for 264 nm channel is presented below. Two injections (beginning and end of run) were made per each level of working standard.

| Working Std. | Conc. IU/ml | No. Inject | Avg. Peak Height |
|---|---|---|---|
| 5T | 1.3440 | 2 | 2.6396 |
| 15T | 4.0320 | 2 | 8.0789 |
| 30T | 8.0640 | 2 | 16.5839 |
| Slope = | 2.07775 | | |
| y-intercept = | −0.20754 | | |
| Corr. Coef. = | 0.99994 | | |

2. The samples should be quantitated by bracketing the standards around the samples.

C. Low pH: Beverage, and Vitamin $D_3$ Emulsion, and Powder Product Calculation

1. Per Weight Basis—IU/Kg: Vitamin $D_3$ (IU/kg)=(C) (V) (1000)#

$$\text{Vitamin } D_3 \text{ (IU/kg)} = \frac{(C)(V)(1000)\#}{(S)(X)}$$

where: C=Vitamin concentration (IU/ml) from standard curve.
V=Volume (ml) of iso-octane to reconstitute extracts.
1000=converts grams to kilograms.
S=Sample size in grams.
X=0.86 for 75° C. saponification factor for thermal isomerization of vitamin $D_3$ to previtamin $D_3$.
=Substitute 100 for 1000 to convert to IU/100 g.

Example: A 12.533 g (S) low pH beverage sample was reconstituted in 2 ml (V) of iso-octane which generated a peak height of 6.2330. The corresponding vitamin $D_3$ concentration (C) obtained from the previously calculated standard curve was 3.0998 IU/ml. The final concentration would be calculated in the following manner:

$$\text{Vitamin } D_3 \text{ (IU/kg)} = \frac{(3.0998)(2)(1000)}{(12.533)(0.86)} = 575 \text{ IU/kg}$$

CALCIUM ASSAY

The Simultaneous Determination of Calcium (Ca) in a Low pH Beverage by ICP-AES Using a High Solids Nebulizer

A. THEORY

1. Inductively coupled plasma atomic emission spectrometry (ICP-AES) is an atomic spectroscopic technique that has several advantages compared to atomic absorption: excellent detection limits, a bread linear calibration range of over four orders of magnitude for most elements, minimal interferences, and the ability to determine several elements in the sample simultaneously under one set of operating conditions. These advantages translate into less sample preparation, calibration, and analysis time for the analyst.

2. The ICP-AES instrument consists of three components: sample introduction device, torchbox, and spectrometer. Most commonly, samples are introduced in the form of solutions which are nebulized (broken into tiny droplets), and passed into the torch with a stream of argon. In the torchbox, 1–2 kW of radio-frequency power is coupled from a copper coil (inductor) into a small region inside a quartz tulle (torch), through which argon flows. The power density in this region is high enough to heat the argon until it ionizes and, since the region is at atmospheric pressure, there are sufficient collisions with other argon atoms to instantly ignite a plasma with a temperature of about 10,000 K.

3. The micrometer-sized droplets from the nebulizer enter the bottom of the torch and pass through the cooler (6000 K), darker, central region of the plasma called the axial channel. Here water is evaporated, and the remaining dry particles of analyte are vaporized and atomized (molecules broken down into atoms) by the heat of the plasma in just a few milliseconds. Excitation and ionization of the outer electrons of the atoms occurs; the intensity of the emission that results from the deexicitation of these atoms and ions is proportional to the concentration of analyte in the original solution. Thus, calibration consists of measuring the intensity of analyte emission for standards of known concentration.

4. Light emitted by the ICP is collected by a lens in the spectrometer and focused onto a diffraction grating which disperses the light into its component wavelengths. The emitted radiation, wavelength resolved, from all the analyte elements is collected simultaneously by several detectors placed in front of the grating and converted into an electrical signal. A data system relates these signals to the concentrations of the elements in the standards and calculates the analyte concentration in the samples.

5. The particular instrument used in this method features a movable entrance slit controlled by a high resolution stepper motor called SAMI (Scanning Accessory for Multielement Instrumentation). Moving the entrance slit slightly changes the angle of incidence upon the grating, and slightly changes the wavelengths incident upon the exit sifts. This feature allows the user to perform background correction in the sample matrix by subtracting the emission background just off the peak center.

6. This method employs a speedy dilution preparation of samples with a surfactant and dilute acid. A special kind of nebulizer called a maximum dissolved solids nebulizer (MDSN), or high-solids nebulizer, is required to provide long term operation without clogging. Because the viscosity of standards and samples is quire different, an internal standard must be used to compensate for the poorer nebulization efficiency of the high solids samples. Cobalt is added to each standard so that they are exactly 20.0 mg/L Co. Calibration consists of measuring the analyte/Co ratio in the standards as a function of analyte concentration. An exact quantity of cobalt is added to each sample so that if they were diluted to 50.0 mL, their cobalt concentration would also be 20.0 mg/L. Note, however, that the analyte/internal standard ratio in the samples will not change with the total volume, and so volumetric ware is not necessary for the sample preparation. When the software asks for the "sample volume" to calculate a dilution factor, the analyst should enter 50 mL, the volume that would make the concentration of cobalt in the samples equal to that in the standards.

MATERIALS

1. Instrument
    a. Inductively Coupled Argon Plasma Emission Spectrometer, ARL Model 3560 or Accuris
    b. Ryton V-groove nebulizer: ARL#173259-0000 or Precision Glass #510-50 only
    c. Spray chamber: ARL#173142-0003 or Precision Glass #110-34 or equivalent d. ICP torch: ARL#139009-0003 or Precision Glass #100-05 or equivalent 2. General Laboratory Equipment/Facilities
   a. Analytical balance
   b. Fume hood
   c. Disposable, flat-bottomed, 50 mL plastic centrifuge tubes with caps (Baxter C3902-14 or equivalent)
   d. Plastic coated rack suitable for holding many centrifuge tubes
   e. 125 mL, 250 mL, and 1L plastic bottles for storing standards: polymethylpentene (PMP) or equivalent
   f. Disposable plastic transfer pipets-3.5 mL capacity
   g. Eppendorf pipet or equivalent, 1000 μL capacity with tips
   h. 50 mL repipetter or equivalent
   i. Plastic dispenser bottle (PMP or equivalent) fitted with a Teflon-constructed dispenser top with adjustable volume between 1–10 mL; dispenser may be fitted to concentrated HCl bottle directly
   j. Magnetic stir plate and Teflon coated magnetic stir bars
   k. 1L and 250 ml volumetric flasks: glass or plastic (PMP or equivalent)
   l. Class A volumetric flasks: 2,4,5,10,15,20,25,40,50 mL
   m. Options: 1 mL digital pipet with tips, Rainin EDP-Plus or 1 mL, glass volumetric pipet or equivalent 3. Chemicals/Standards Unless otherwise noted, the following chemicals should be stored at room temperature. Their expiration date is one year after the date they are first opened. Upon expiration the chemicals must be either discarded or re-evaluated.
   a. High purity stock standard solutions (NIST or NIST-traceable) 10,000 mg/L Ca, 10,000 mg/L Co, 1000 mg/L Co. These stock standard solutions expire on the date given by the manufacturer.
   b. Hydrochloric acid, J. T. Baker BIA-grade or equivalent
   c. Triton X-100, Kodak scintillation-grade or equivalent
   d. Argon gas, minimum 99.996% purity
   e. High purity water, Millipore-treated or equivalent

C. INSTRUMENTAL OPERATING CONDITIONS

1. The wavelengths that have been used are listed in the table below. The instrument should be installed with identical channels if possible because the sensitivity of the line and the possibility of interferences can change if a different line is employed for analysis.

| ELEMENT | WAVELENGTH (nm) | TYPE | ORDER |
|---------|-----------------|------|-------|
| Ca      | 317.93          | ion  | 2     |

2. Typical ranges of operating conditions for the ARL 3560 are listed below.

| | | |
|---|---|---|
| a. | Incident power: | 1200–1400 watts |
| b. | Reflected power: | <5 watts |
| c. | Snout argon gas flow: | on |
| d. | Coolant argon pressure: | 30–40 psi |
| e. | Plasma argon pressure: | 20–30 psi |
| f. | Nebulizer argon pressure: | 30–46 psi (~0.6–0.7 L/minute if a mass flow controller or other type of flowmeter is used to regulate flow) |
| g. | Peristaltic pump flow rate: | dial setting which corresponds to ~2.5 mL/min. (depends on make and model of pump) |
| h. | Peristaltic pump tubing: red/red P.V.C., Marprene, or equivalent | 1.12 mm I.D. |

3. Software parameters: These are stored in the TASK files which perform calibration and sample measurement and must not be altered.
   a) Integrations (on-peak): three 5 second integrations per sample
   b) Integrations (off-peak): two 5 second integrations taken at −80 SAMI units off peak center

D. STANDARD AND SOLUTION PREPARATION

Store at room temperature unless otherwise noted.

1. 2% HCl rinse: Mix concentrated HCl with high purity water in the approximate ratio of 20 mL acid to 1000 mL total volume of solution. Use a plastic container of a size appropriate to the volume of solution prepared. For example, to prepare 20 L of 2% HCl, fill a 21L carboy with high purity water to the 20L mark and add 400 mL HCl to the water. Expiration: 6 months.

2. Triton X-100 solution (approximately 5%): Add about 700 mL high purity water to a 1L plastic bottle containing a Teflon-coated stirring bar. Place the bottle on a magnetic stirrer and begin stirring at a moderate speed. Slowly add 50 mL Triton X-100 from a graduated cylinder. When the Triton is dissolved, fill the bottle approximately 1000 mL with high purity water. Transfer to 1L plastic bottle fitted with a Teflon-constructed dispenser with adjustable volume from 1–10 mL. Expiration: 6 months.

3. Traditional standard solution preparation: Prepare 1 liter of the appropriate standard solution. Add the indicated amount of 10,000 or 1000 mg/L stock standard solution to a 1L volumetric flask using a Class A pipet. Then add approximately 800 mL of high purity water, 2.00 mL of 10,000 mg/L cobalt internal standard (Class A pipet), and 20 mL (repipetter or dispenser) of hydrochloric acid to each flask. Add 50 mL of Triton X-100 solution from the dispenser to each flask and then fill the flasks to volume with high purity water, slowly to avoid forming suds. Agitate well and transfer to clean, dry 1 liter storage bottles. Dispense as needed into 125 mL storage bottles to use at the instrument. Expiration: 6 months.

4. Standard blank solution: Prepare 1 liter of a standard blank at the same time, and from the same reagent batches, as the above standards. Add 800 mL high purity water to a 1L volumetric flask; 2.00 mL of 10,000 mg/L cobalt internal standard (Class A pipet), and 20 mL (repipetter) of hydrochloric acid to the flask. Add 50 mL of Triton X-100 solution from the dispenser to the flask and then fill the flask to volume with high purity water, slowly to avoid forming suds. Agitate well and transfer to a clean, dry 1 liter storage bottle. Dispense as needed into 125 mL storage bottles to use at the instrument. Expiration: 6 months.

5. Internal standard reference blank solution (ISRB): Prepare 1 liter of an ISRB at the same time, and from the same reagent batches, as the above standards. Add 800 mL high purity water to a 1L volumetric flask and 20 mL (repipetter) of hydrochloric acid to the flask. Add 50 mL of Triton X-100 solution from the dispenser to the flask and then fill the flask to volume with high purity water, slowly to avoid forming suds. Agitate well and transfer to a clean, dry 1 liter storage bottle. Dispense as needed into 125 mL storage bottles to use at the instrument. Expiration: 6 months. Note that the ISRB does not contain cobalt, but the standard blank does. The ISRB is analyzed before any standards or samples; the purpose is to subtract the intensity of analytes found in the reagents (Triton X-100 solution, HCl, and water) from the analyte intensities found in the standards and samples.

E. PROCEDURE

1. Standard Handling
   a. All bottles used for storage of standard solutions must first be soaked in 10% (v/v) HCl for a minimum of three hours, followed by multiple rinses with high purity water. Air dry or rinse several times with the standard. When reusing the bottles for a new batch of the same standard, no acid soak is necessary—simply rinse several times with high purity water and then several times with small portions of the fresh standard.
   b. As the working standards in the 125 mL bottles are used up, simply refill the bottles from the 1 L standards prepared in D. 3.
   c. Because there are many samples, the most efficient way to add the cobalt internal standard to the samples is with a 1 mL digital pipet.

2. Sample Preparation
   a. Refill the reagent containers before preparing samples so that the same batch of reagents can be used for all samples and the blank.
   b. Remove the caps and arrange the empty 50 mL tubes, with labels, in the rack beginning with the sample blank and two tubes for each sample.
   c. Transfer sample to a plastic storage container. Place these containers directly on a magnetic stirring plate and add a Teflon coated stirring bar. Set the stirrer at an intermediate speed. After a minimum of one minute of agitation begin to withdraw the sample for weighing with a disposable plastic transfer pipet.
   d. Carefully weigh and record to the nearest 0.0001 g, 5 g of sample into the plastic tubes. The sample blank tube is left empty at this point. Add the following reagents to each tube, including the blank, in this exact order:
      (1) Add 2.5 mL of Triton X-100 solution using the dispenser bottle.
      (2) Add approximately 45 mL of high purity water
      (3) Add 1.00 mL of the 1000 mg/L cobalt internal standard with either a calibrated digital pipet (preferred) or a Class A pipet.
      (4) Add 1 mL of concentrated hydrochloric acid with an Eppendorf pipet or from a Teflon dispenser bottle.
      (5) Add high purity water until the total volume in each tube is approximately 50 mL. Put the caps on and shake the tubes thoroughly.

3. Instrumental Analysis
   a. The following instructions refer to some general characteristics of the PLASMAVISION software, which is currently used on all instruments running this method, but no attempt has made to describe specific key sequences needed to perform these procedures, since that information is provided in training. Equivalent operations must be performed with other versions of the software.
   b. Turn on the plasma and allow a thirty minute warm-up time before calibration. Turn on the computer and printer and start the software. Begin pumping 2% HCl rinse solution through the nebulizer.
   c. Perform an instrument configuration before the first calibration is made for each 8-hour shift. This will check computer-instrument communications and check the SAMI motor. Watch the motor to be sure that it turns properly.
   d. Check the optical alignment using the 150 mg/L calcium standard. This procedure will insure that the SAMI motor is operating properly and that the calibration will always be performed near the exact center of each analyte peak. Perform this procedure before the first calibration is made, once during each 8-hour shift. Choose appropriate setup options and then run the profile. The measured peak centers for the element to be measured must be within ±6 SAMI units of the current SAMI profile position. If this result is not obtained, consult the supervisor: either a new default SAMI profile position needs to defined, or the instrument requires service.
   e. Select the appropriate task and the appropriate calibration sequence file name and begin calibration. Aspirate the standard solutions into the plasma starting with the ISRB solution prepared in D.5. The software prompts for each standard by name. Be alert to any error messages. If an error occurs, write down the message and consult the supervisor. After the last standard has been run, save the data and have the software calculate a linear regression for each element. Print the calibration data, which summarizes the element intensities in each standard, the correlation coefficient, and the calculated concentrations of the elements in each standard.
   f. Enter the section of the software to analyze the samples. Set the print options to print whatever documentation is required. Select a name for the file that will store sample results; if no file name is chosen, the program will store the data under the task file name by default.
   g. Shake the samples immediately before introduction into the ICP.
   h. HIT THE ENTER OR RETURN KEY AFTER ENTERING THE WEIGHT, VOLUME AND NAME OF THE SAMPLE. Note that the PLASMAVISION software prompts for the sample weight and volume before the sample is introduced, and the sample name after it has been analyzed. The dilution volume for samples will always be entered as 50 mL, regardless of the actual volume in the sample tube.
   i. Make sure that the sample introduction tube is placed in the 2% HCl rinse solution for at least 2–3 seconds between samples. Analyze the standards and the samples in the following order:
      (1) Analyze the intermediate check standard solutions.
      (2) Analyze the "reagent blank" (or sample blank, contains cobalt). The intensities of the analytes in this blank will be subtracted automatically from the intensities found in the samples.
      (3) Analyze each sample in duplicate.
   j. Results can be reported in any convenient concentration units, depending upon how the tasks are programmed. Note: in cases in which the analyst has entered the calibration standards into the task as "mg/L" and has entered the dilution volume as "50 mL" and the sample weight in grams, the sample results will be in units of μg/g. The actual printout will show whatever units are programmed into the task for each element. The unit "μg/g" is preferred to "ppm" for reporting sample results because the latter term is ambiguous. In laboratories where sample results for this method are commonly reported as "ppm", it must be understood that this really means "micrograms of analyte per gram of sample."

VITAMIN C (L-ASCORBIC ACID) DETERMINATION

A. SAMPLE SIZE AND PRODUCT APPLICABILITY

Samples should be as uniform and representative of the product as possible. Sampling should be performed immediately after a gentle mixing or stirring to prevent inaccurate sampling due to stratification. All sample weights must be recorded to at least three significant figures.

Sample sizes for low pH beverages are calculated from the following equation.

$$\text{Sample size} = 350/E$$

where:

Sample Size is the theoretical sample size, in grams; E is the expected ascorbic acid concentration in milligrams per liter or kilogram, respectively, as is, and; 350 is the desired amount, in micrograms (mcg), of ascorbic acid in the sample preparation. The net conversion factor for micrograms to milligrams and kilograms to grams is unity.

B. THEORY

In this method the amount of L-ascorbic acid present in the sample is determined by coulometric titration. A coulometric method of analysis measures the quantity of electricity required to carry out a chemical reaction. If the reaction is 100% efficient, the passage of one Faraday of electricity will cause the reaction of one equivalent weight.

In this case, iodine is coulometrically generated from iodide. The iodine then oxidizes the L-ascorbic acid to dehydroascorbic acid. When enough iodine has been produced to oxidize all the L-ascorbic acid in the sample, an excess of iodine will occur. This excess of iodine signals the equivalence point, and is detected by two constant potential electrodes. The quantity of electricity used is given by the product of current times the time to reach the end point of the coulometric titration. Thus the amount of iodine used is equal to the number of equivalents of L-ascorbic acid, and the amount of L-ascorbic acid can be calculated.

Trichloroacetic acid is added to the sample to precipitate the protein and to maintain the acidic condition necessary for a quantitative reaction.

C. APPARATUS

Analytical Balance
Beakers, 100 ml, graduated
Brinkmann E585 Polarizer
Cable for Double Platinum Wire Electrode, Brinkmann cat. no. 20-97-738-8, or equivalent
Cables for Platinum Foil Electrodes, Brinkmann cat. no. 20-97-770-1 and 20-00-853-9, or equivalent
Chart Paper
Desiccator
Disposable Pipets
Disposable tips for pipettor
Double Platinum Wire Electrode, Brinkmann cat. no. 20-92-350-4, or equivalent
Electrode Holder
Eppendorf pipet or equivalent, 200 mcl
Isolation Tube, outer diameter 20 mm, 125 mm long, Pore Size C, Ace Glass Company cat. no. 7209-16; OR outer diameter 12 mm, 125 mm long, Pore Size E, Ace cat. no. 7209-10. Size of isolation tube depends on size of electrodes used.
Keithly Model 225 Constant Current Source OR Keithly Model 220 Constant Current Source
Magnetic Stir Plate
Pipettor; 5 ml—Oxford, Wheaton, Eppendorf, or Finnipepette
Pipetrot or dispenser; 10 ml and 30 ml—Oxford, Wheateon, Lab Industries or equivalent
Platinum Foil Electrodes, (2), Brinkmann cat. no. 20-92-110-2, or equivalent
Sample vials, 5 ml with screw caps
Shields: yellow or clear shields with a cutoff of 385 nanometers
Strip Chart Recorder; Kipp & Zonen or equivalent
Teflon-coated Stir Bars
Ultrasonic Bath
Vacuum Flask, 2,000 mL
Volumetric flasks, 100, 500 ml, 1000 ml with stoppers

D. REAGENTS

I. CHEMICALS

L(+) ascorbic acid (USP Reference Standard, Official Lot); store in a desiccator
Metaphosphoric acid; ACS or equivalent
Potassium iodide; ACS or equivalent
Sodium sulfate, anhydrous granular; ACS or equivalent
Trichloroacetic acid; ACS or equivalent

II. SOLUTIONS

NOTE: All solutions, samples and standards must be prepared and stored under UV shielded or yellow shielded lighting unless otherwise stated (see APPARATUS).

NOTE: Degassed water should be used for the 0.1M potassium iodide solution to prevent air oxidation of $I^-$ to $I_2$. Degas water by placing deionized water into a vacuum flask, and placing it under vacuum for 15 minutes with sonication.

1. Potassium Iodide (0.1M) Weigh 8.3 (±0.5) g of potassium iodide into a 500 ml volumetric flask. Dissolve and dilute to volume with degassed, deionized water. Store in a tightly stoppered brown bottle at room temperature. Do not store for more than one (1) week. Discard if solution acquires a yellow tinge.

2. L-Ascorbic Acid Standard (2000 mg/L) Store standard bottle in a desiccator to prevent moisture absorption. Weigh accurately 0.200 (±0.0005) g and transfer quantitatively to a 100 ml volumetric flask. Dissolve and dilute to volume with 3% metaphosphoric acid. The standard can be made fresh just before use each day, or can be stored in small vials in the freezer. Standard stored in the freezer is good for two months.

3. Trichloroacetic Acid (1M) Weigh 163 (±0.5) g of trichloroacetic acid into a I liter volumetric flask. Add 500 ml degassed deionized water. Swirl until dissolved, then dilute to volume. This reagent may be stored for one month at room temperature.

4. Sodium Sulfate (1M) Weigh 142 (±0.5) g of sodium sulfate into a 1 liter volumetric flask. Add approximately 750 ml of deionized water and mix until dissolved. Dilute to volume with deionized water. This reagent may be stored for six months at room temperature.

5. Metaphosphoric Acid (3%) Accurately weigh 15.0 (±0.10) g of metaphosphoric acid and quantitatively transfer to a 500 ml volumetric flask. Add approximately 250 ml deionized water and swirl until Metaphosphoric acid is dissolved. Dilute to volume with water. This solution may be stored for one week under refrigeration (2°–8° C.).

E. PROCEDURE

Instrument Settings—FIGS. 8, 9, 10 and 11.

| a. | Recorder | Chart speed/input | 1 mm/second or 5 cm/min, depending on chart recorder/1 volt |
|---|---|---|---|
| b. | Polarizer E585 | Constant potential sensitivity | 150 mV 10 microamps |
| c. | Keithly Constant Current Source | | 1.56 ma |

1. Fill the isolation tube containing the cathode electrode with 1M sodium sulfate. The sodium sulfate continuously moves from the isolation tube through the glass frit into the sample solution and must be frequently replenished.

2. An instrument check should be done at the start of each day. Using an Eppendorf pipet (or equivalent), pipet 200 microliters of the 2000 mg/L L-ascorbic acid standard into a 100 ml beaker. Follow steps 5 through 12 of the procedure. Follow steps 1 through 4 of the calculations. Compare the experimentally determined concentration to the theoretical concentration. The results should be within 4% of the expected value. If not, run another instrument check using fresh reagents and standard. If the experimental result still differs by more than 4% from the expected standard value, consult the method supervisor.

3. Agitate samples well before and during sampling. Liquid samples must be freshly opened. Analyses must be completed within 20 minutes after the container is opened. Samples are weighed directly into the beaker unless otherwise stated.

4. While swirling the sample, add 5.0 (±0.1) ml of 1M trichloroacetic acid (TCA) to the sample. Swirl for 30 seconds to completely precipitate the protein.

5. Add 30.0 (±0.5) ml of 0.1M potassium iodide to the sample.

6. Add degassed deionized water to approximately the 60 ml mark.

7. Add a stir bar. Lower the electrodes into the sample solution. Make sure that all the electrodes are immersed. The sodium sulfate level in the isolation tube must be at least 2 cm above the sample level. Adjust the magnetic stirrer speed so that stirring is vigorous but no air is entrained.

8. Switch the chart recorder on. Switch the polarizer on. Adjust the base line of the chart recorder to 10% of full scale.

9. Switch the constant current source on.

10. Titrate until excess iodine is produced, indicated by a rising current curve. Stop the titration when the rising current curve has reached at least 70% of full scale on the chart recorder paper.

11. Switch the recorder chart speed to off and the constant current source to standby.

12. Remove the electrodes from the sample and rinse well with deionized water.

F. CALCULATIONS

Figure 12:
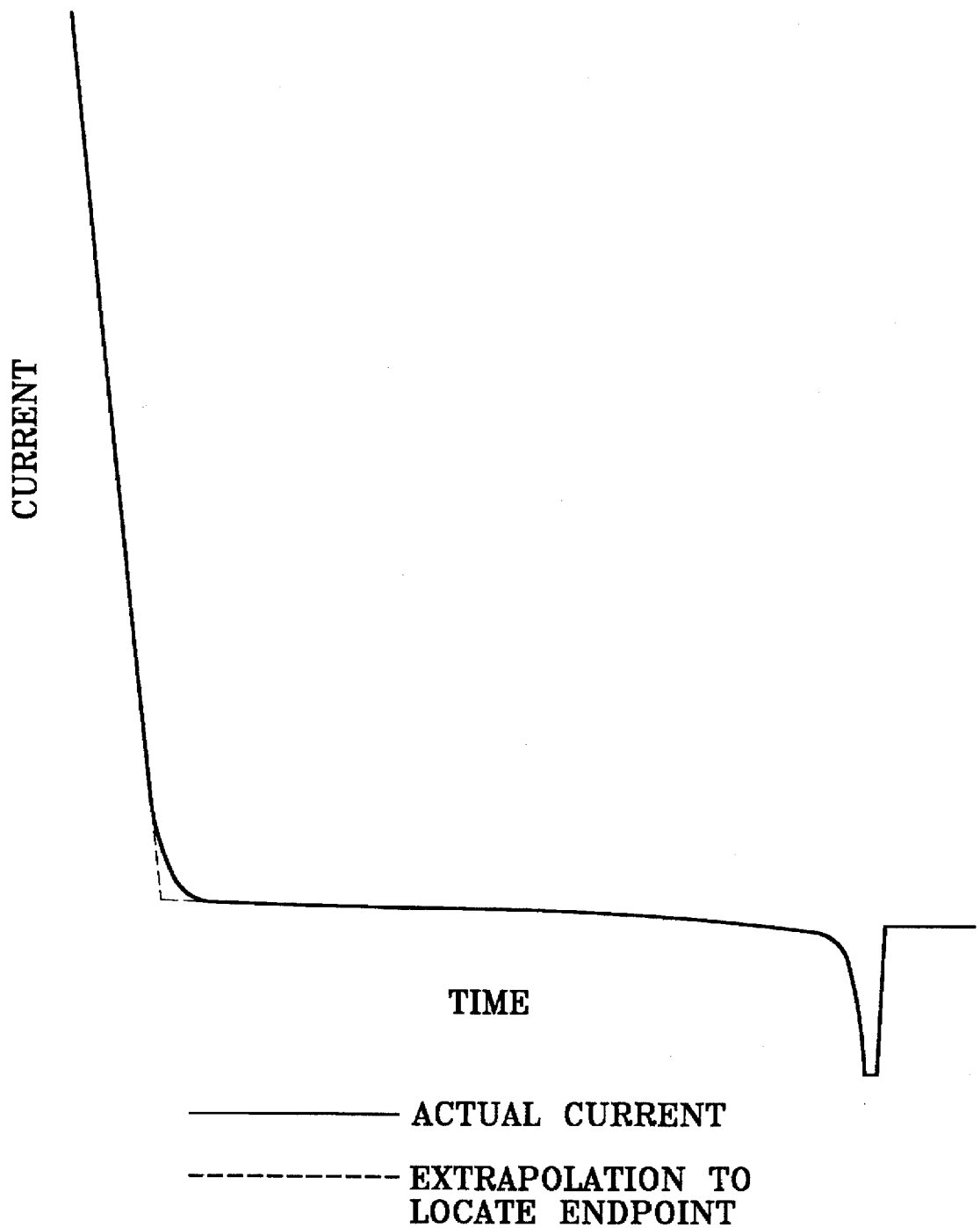

1. Extrapolate the linear portion of the rising current curve to the base line to locate the end point. The portion of the curve between 70% and 30% of full scale will be linear. (FIG. 12).

2. Count the number of centimeters from start of titration to the end point to the nearest 0.1 centimeter.

3. Convert this distance to seconds of titration time.

4. Calculate the amount of L-ascorbic acid present in the sample by the following formula:

$$C = \frac{m \times i \times t}{n \times s \times F} = \frac{i \times t \times R}{s}$$

Where:

C=concentration of L-ascorbic acid in mg/l or mg/kg (mcg/ml=mg/l and mcg/g=mg/Kg)

m=176 (gram molecular weight of L-ascorbic acid)

n=2 (change in valence)

i=current in milliamps t=time in seconds

F=96,487 coulombs/equivalent

R=proportionality constant for m,n and $$F = 0.912 \frac{mcg}{mA\text{-}sec}$$

s=sample size in g

EXAMPLE: Assume a 3.0 g sample of a low pH beverage was analyzed and the measured length of titration on the strip chart was 19.0 cm. Chart speed was 1 mm/sec. The current during the titration was 1.56 mA $$C = \frac{R \times t \times i}{s}$$

$i = 1.56$ mA
$s = 3.0$ g
$R = 0.912$ mcg/mA-sec $$t = \frac{19 \text{ cm}}{1} \times \frac{1 \text{ sec}}{1 \text{ mm}} \times \frac{10 \text{ mm}}{1 \text{ cm}} = 190 \text{ sec}$$

$$C = \frac{(1.56 \text{ mA}) \times (0.912 \text{ mcg/mA-sec}) \times (190 \text{ sec})}{3.0 \text{ g}}$$

= 90 mcg/g

= 90 mg/Kg

SELECTION OF INGREDIENTS USED IN PRACTICING THE INVENTION

The present invention provides high levels of calcium and vitamin D in a carbonated beverage, a noncarbonated beverage, a liquid beverage concentrate, a powdered beverage concentrate, a powdered beverage additive, beverages containing a powdered beverage concentrate or additive, or a calcium supplement. As used herein and in the claims the terms "liquid nutritional product" and "beverage" are understood to be synonymous. As used herein and in the claims a "low pH beverage" is understood to refer to a beverage having a pH of less than 4.6. Trial batches of low calorie lemon lime, orange, peach, and wild cherry flavored prototype carbonated beverages have been manufactured in accordance with the present invention. The prototype beverages were manufactured by preparing a beverage concentrate, then blending the beverage concentrate with treated water. The blends where then carbonated and filled into standard 12 ounce soda aluminum cans. (Soda aluminum cans are coated in accordance with accepted industry standards to substantially reduce migration of aluminum into the contents of the can.)

Calcium Source. As used herein and in the claims the term "calcium" used alone refers to elemental calcium, the term "calcium salt" refers to a chemical composition containing elemental calcium, and "calcium source" refers to calcium and/or a calcium salt. The calcium salt used in preferred embodiments of the present invention is Calcium Glycerophosphate (CaGP) which is generally recognized as safe (GRAS) by the United States Food and Drug Administration (FDA) (21 CFR 170.3). Another reason for selecting CaGP is that, as already disclosed above in the background section, it is one of the ten calcium compounds recognized by FDA as safe and lawful for use in a dietary supplement or as a nutrient supplement for osteoporosis. However; any other suitable calcium source, such as calcium citrate malate that would be soluble at a pH of about 3.5–4.5 could be employed in the practice of the present invention.

Calcium glycerophosphate (CaGP) can be described as a white, odorless, almost tasteless powder. Its solubility in water increases in the presence of citric and lactic acids, as stated in the Merck Index. The CaGP used in the trial batches was FCC III grade and was produced by Dr. Paul Lohman GmbH, Emmerthal, Germany and is distributed by Gallard Schlesinger Industries, Inc., Carle Place, N.Y., 11514, USA.

Another reason for selecting CaGP is its excellent calcium bioavailability. Churella et al., "RELATIVE CALCIUM (CA) BIOAVAILABILITY OF CA SALTS USED IN INFANT FORMULAS", THE FASEB JOURNAL, 4(3):A788 (1990) reports a study which determined the calcium bioavailability of four calcium salts. Rats were fed various diets containing different calcium salts for three weeks. At the end of the study, the right femur was removed and tested for calcium. As compared to a control, the relative calcium bioavailability was as follows: tricalcium phosphate 110%, calcium citrate 110% and CaGP 106%. Furthermore, studies reported by Hanning et al, "Efficacy of calcium glycerophosphate vs conventional mineral salts for total parenteral nutrition in low-birth-weight infants: a randomized clinical trial[1-3]", AMERICAN JOURNAL OF CLINICAL NUTRITION, 54: 903–908 (1991), and Draper et. al., "Calcium Glycerophosphate as a Source of Calcium and Phosphorous in Total Parenteral Nutrition Solutions", JOURNAL OF PARENTERAL AND ENTERAL NUTRITION, 15(2): 176–180 (1991) showed in low birth weight infants and piglets, respectively, that CaGP is as effective as calcium gluconate as a source of calcium in total parenteral nutrition (TPN) solutions and could be used to prevent under mineralized bones in low birth weight infants.

Yet another reason for selecting CaGP was its high solubility which facilitates a larger calcium intake per serving. A number of calcium salts were evaluated for their functionality in the liquid nutritional product of the present invention: dicalcium phosphate, monocalcium phosphate, calcium chloride, tricalcium phosphate, calcium citrate, calcium carbonate, CaGP, and D-gluconic acid (hemicalcium salt). Aqueous solutions containing 500 mg of calcium per 237 mL (8 oz.) serving (2110 ppm) were prepared and the pH was adjusted to pH 3.5 and pH 5.0. Results indicated that solubility of calcium salts varied and only calcium carbonate, calcium chloride, CaGP, and D-Gluconic acid, remained soluble at pH 3.5 for at least one month. In this evaluation solubility was determined by a visual examination. At pH 5.0 all samples formed crystals over time. The results of this solubility study are presented in Table 3.

TABLE 3

SOLUBILITY OF CALCIUM SOURCES
(Solutions at 500 mg calcium per 237 mL)

| Salt | At Time of Manufacture | | 1 MONTH | |
|---|---|---|---|---|
| | pH 3.5 | pH 5.0 | pH 3.5 | pH 5.0 |
| Dicalcium Phosphate | insoluble | insoluble | insoluble | insoluble |
| Monocalcium Phosphate | insoluble | insoluble | insoluble | insoluble |
| Calcium Chloride | soluble | soluble | soluble | insoluble |
| Tricalcium Phosphate | insoluble | insoluble | insoluble | insoluble |
| Calcium Citrate | insoluble | insoluble | insoluble | insoluble |
| Calcium Carbonate | soluble | partially Soluble | soluble | insoluble |
| CaGP | soluble | soluble | soluble | insoluble |
| D-Gluconic-Acid* | soluble | soluble | soluble | partially Soluble |

*Hemicalcium salt

Experiments were repeated with calcium carbonate, CaGP, and calcium chloride in a complete liquid nutritional product matrix, i.e., in conjunction with aspartame, a flavor system and vitamin C. The pH range evaluated was 3.5–4.5. At the lower end of the pH range all calcium sources were soluble at time of manufacture. After one month it was observed that as the pH increased, calcium carbonate and CaGP formed crystals, worse in the case of calcium carbonate. In addition, it appeared that the CaGP had a synergistic effect with aspartame regarding sweetness. Calcium chloride was completely soluble throughout the pH range but its bitter flavor made it unacceptable for the liquid nutritional product of the present invention application. Calcium lactate was evaluated in subsequent experiments. Although its solubility was excellent it provided astringent and mineral salt-type notes to the taste of the beverage that made it undesirable.

Still another reason for selecting CaGP is the fact that a beverage matrix containing this calcium salt requires the addition of less acid to achieve a pH below 4.0. Acidity is desired in the liquid nutritional product of the present invention for several reasons such as: to maintain the calcium salt solubility, to complement flavor, to control microbial growth, and to enhance the role of preservatives, specifically potassium benzoate or sodium benzoate. On the other hand, too much acidity can result in increased tartness and sourness that make the product undesirable from a sensory point of view. When calcium salts are added to the liquid nutritional product of the present invention, the solution resists changes in pH and more acid is needed to bring down the pH than in commercially available sodas with no calcium fortification. Aqueous solutions of various calcium salts were prepared to deliver 500 mg of elemental calcium per 12 oz. serving (1408 ppm) and the pH adjusted to pH 3.5 with citric acid. Titratable acidity was determined by measuring the amount of 0.1N NaOH needed to raise the pH to 8.3 in a 40 g sample containing 1,409 mg/Kg of a calcium source. The results presented in TABLE 4 indicate that, with the exception of calcium chloride, CaGP was the calcium salt that had the lowest titratable acidity. Titratable acidity is an indication of the total acidity of a beverage.

TABLE 4

TITRABABLE ACIDITY OF CALCIUM SOURCES

| Calcium Source | Titratable acidity mL of 0.1N NaOH |
| --- | --- |
| Calcium Chloride | 0.7 |
| CaGP | 43.5 |
| Calcium Lactate | 47.1 |
| Tricalcium Phosphate | 48.6 |
| Calcium Citrate Malate | 53.2 |
| Calcium Citrate | 57.5 |
| Calcium Hydroxide | 60.6 |
| Calcium Carbonate | 61.4 |

Calcium glycerophosphate (CaGP) is created by the reaction of glycerophosphate, a weak acid with pKf=6.1, with the strong base calcium hydroxide. GaGP binds calcium with an approximate formation constant of 1.7. CaGP, when dissolved in water, dissociates readily to provide "free" calcium ions and protonated glycerophosphate species. Acid-base buffering by monoprotonated glycerophosphate is effective only within the pH range from 4.1 to 8.1 (refer to the Henderson-Hasselback equation), and thus, GP exhibits insignificant buffering capacity at pH=3.6. On the other hand, anions, such as malate, tartrate, propionate or succinate, do provide buffer capacity at pH=3.6, and accordingly require more base or acid than GP for final adjustment of pH.

Yet another reason for selecting CaGP is the low aluminum content in commercially available CaGP. It has been theorized that chronic use of calcium supplements which have significant aluminum contents may constitute unnecessary metal exposure. Whiting, "Safety of Some Calcium Supplements Questioned", NUTRITION REVIEWS, 52(3): 95–97 (1994). The aluminum content of some calcium sources is presented in TABLE 5.

TABLE 5

ALUMINUM CONTENT OF CALCIUM SOURCES

| Calcium Source | Aluminum Content in parts per million (ppm) |
| --- | --- |
| CaGP | 4.55 |
| Calcium Hydroxide | 300–400 |
| $CaCO_3$ (from fossil shell) | $4,400^2$ |
| $CaCO_3$ (from Dolomite) | $171–315^2$ |

[1]Values determined by analysis of commercially available compounds.
[2]Values from Whiting article.

It has been suggested that calcium citrate may play a role in enhancing aluminum absorption from food, potentially resulting in toxic serum and urinary aluminum levels. Sakhaee et al., have successfully demonstrated however, that the provision of calcium citrate alone without aluminum—containing drugs does not pose a risk of aluminum toxicity in subjects with normally functioning kidneys. Sakhee et al., "Calcium citrate without aluminum antacids does not cause aluminum retention in patients with functioning kidneys," BONE AND MINERAL, 20: 87–97 (1993).

Vitamin D. As used herein and in the claims the terms "vitamin D" and "various forms of vitamin D" are understood to refer to vitamin D, cholecalciferol ($D_3$), ergocalciferol ($D_2$) and its biologically active metabolites and precursors such as, 1α, 25-$(OH)_2$ vitamin D; 25 OH vitamin D, its biological precursor; and 1 a, hydroxyvitamin D, and analogues of the dihydroxy compound. These materials promote intestinal absorption of calcium, contribute to plasma calcium regulation by acting on the remodeling processes of accretion and resorption and stimulate reabsorption of calcium by the kidney. While the form of vitamin $D_3$ used in the following examples, prototypes and experiments is cholecalciferol, it is understood that any of the various forms of vitamin D may be used in practicing the present invention, but vitamin $D_3$ is preferred in embodiments which are liquids.

Dietary calcium and vitamin D are the natural mediators against bone loss. Vitamin D acts directly on bone cells (osteoblasts, osteoclasts) to alter bone mass. It also promotes gut uptake of calcium. Human skin activates pre-vitamin D molecules when exposed to ultra violet irradiation. In the summer, 15 minutes exposure to sunlight is sufficient to maintain adequate vitamin D levels. On the other hand, during winter, all day exposure to sunlight will produce negligible conversion of vitamin D. The thinner skin associated with aging is a less effective converter than the youthful skin.

The addition of vitamin D to the liquid nutritional product of the present invention was difficult because this is an oil soluble vitamin whereas both the beverage concentrate and the beverage of the present invention are aqueous solutions. A number of possible methods to overcome the immiscibility of these two phases were evaluated. The results of these efforts are related below, and batch numbers are sequential throughout the following studies.

There were two major obstacles to overcome regarding the incorporation of vitamin $D_3$ in the present invention: (t) the initial processing loss of vitamin $D_3$; and (2) the stability of vitamin $D_3$ over the shelf life of the product. To compare the initial processing loss and stability of vitamin $D_3$ Of each variable with successive batches, two criteria were routinely measured: (1) % recovery of vitamin $D_3$ at 0-time; and (2) half life of vitamin $D_3$ ($t_{1/2}$).

The % recovery of vitamin $D_3$ of each batch was calculated by dividing the 0-time vitamin $D_3$ result by the theoretical fortification of each batch times 100%. (See Table 6). As used herein "theoretical fortification" refers to amount of vitamin $D_3$ added to the product. As used herein "0-time" refers to the time of initial vitamin $D_3$ analysis of the product. In Table 6, "% Recovery" is the percentage of theoretical fortification of vitamin $D_3$ remaining in the product after initial processing loss. Only batch 31 did not have the 0-time vitamin $D_3$ determined. Therefore, a projected result for this batch was extrapolated from the negative exponential regression curve generated from the stability data.

TABLE 6

0-TIME VITAMIN $D_3$ RESULTS VERSUS THEORETICAL FORTIFICATION

| BATCH | 0-TIME | THEORETICAL | % RECOVERY |
| --- | --- | --- | --- |
| 1 | 440 | 950 | 46.3% |
| 2 | 405 | 950 | 42.6% |
| 3 | 450 | 950 | 47.4% |
| | | Mean for batches 1–3 | 45.4% |
| 4 | 249 | 635 | 39.1% |
| 5 | 283 | 635 | 44.6% |

TABLE 6-continued

0-TIME VITAMIN $D_3$ RESULTS VERSUS THEORETICAL FORTIFICATION

| BATCH | 0-TIME | THEORET-ICAL | | % RECOVERY |
|---|---|---|---|---|
| 6 | 294 | 633 | | 46.4% |
| | | | Mean for batches 4–6 | 43.4% |
| 7 | 371 | 483 | | 76.8% |
| 8 | 328 | 634 | | 51.7% |
| 9 | 308 | 618 | | 49.8% |
| | | | Mean for batches 7–9 | 59.4% |
| 10 | 548 | 841 | | 65.2% |
| 11 | 696 | 844 | | 82.5% |
| 12 | 680 | 843 | | 80.7% |
| 13 | 691 | 844 | | 81.9% |
| 14 | 546 | 842 | | 64.9% |
| 15 | 649 | 845 | | 76.8% |
| 16 | 679 | 844 | | 80.5% |
| 17 | 681 | 844 | | 80.7% |
| | | | Mean for batches 10–17 | 76.7% |
| 18 | 752 | 916 | | 82.1% |
| 19 | 678 | 915 | | 74.1% |
| 20 | 802 | 916 (control batch) | | 87.6% |
| 21 | 784 | 917 | | 85.5% |
| 22 | 491 | 917 | | 53.5% |
| 23 | 796 | 916 | | 86.9% |
| 24 | 798 | 916 | | 87.1% |
| | | | Mean for batches 18–19 & 21–24 | 78.2% |
| 25 | 473 | 826 | | 57.3% |
| 26 | 526 | 825 | | 63.8% |
| 27 | 539 | 825 | | 65.3% |
| 28 | 633 | 825 | | 76.7% |
| 29 | 517 | 793 (control batch) | | 65.2% |
| 30 | 576 | 823 | | 70.0% |
| | | | Mean for batches 25–28 & 30 | 66.6% |
| 31 | 786*** | 840 | | 93.6% |

***No Data Available - Extrapolated From the Exponential Regression Curve

To better characterize the stability of vitamin $D_3$ over time in all the batches, the Henri-Michaelis-Menton exponential equation was employed. The vitamin $D_3$ results (IU/KG) for each variable was plotted versus time (Day) and a regression curve was fitted through the data using the following equation:

$$[D] = [D_o]e^{-kt}$$

Where:

[D]=Vitamin $D_3$ concentration (IU/KG) at time (t).
[$D_o$]=Vitamin $D_3$ concentration (IU/KG) at 0-time,
e=Exponential
k=Rate constant (rate of loss of vitamin $D_3$ over time)
t=Time (days)

Stability was defined as the amount of time (days) that would be required for the initial concentration of vitamin $D_3$ to be reduced one half. This was termed half-life ($t_{1/2}$). The more stable the vitamin $D_3$ in a particular formulation, the longer it would take for the initial concentration to be reduced by one half. Rearranging the previous equation and making the appropriate substitutions, the half-life of vitamin $D_3$ in a particular variable could be expressed as:

$t_{1/2}=\ln 2/k$ $t_{1/2}$=Time (days) required for vitamin $D_3$ to be reduced by one half of the initial concentration.
ln=Natural log.
k=First order rate constant (rate of loss of vitamin $D_3$ over time).

The various batches are described in the following text. For convenience, the batch numbers are sequential. In addition, the actual vitamin $D_3$ data at each time point for each respective variable are presented in Tables 8, 10, 12, 13, 14, 16 and 17. The correlation coefficients, initial vitamin $D_3$ concentration [$D_o$], first order rate constants (k), and vitamin $D_3$ half lives ($t_{1/2}$) are also presented in Tables 8, 10, 12, 13, 14, 16 and 17 and should be referred to during the discussion.

A detailed discussion of each variable will not be presented since such a presentation would be quite lengthy. Rather an overview of various batches grouped with respect to the main variables that were studied will be discussed.

a. Use of a Water Dispersable Form of Vitamin $D_3$

Early in the development of the present invention an evaluation was made of a water dispersable vitamin $D_3$ spray dried on a dicalcium phosphate and gum acacia carrier. The water dispersible vitamin $D_3$ used in this evaluation was a DRY VITAMIN $D_3$ Type 100-DS purchased from Roche Vitamins and Fine Chemicals, a division of Hoffman-LaRoche, Inc., Nutley, N.J., U.S.A., which contains vitamin $D_3$ (cholecalciferol USP-FCC), dicalcium phosphate, gum acacia, coconut oil, BHT, lactose, silicon dioxide, sodium benzoate and sorbic acid. It is a white powder and contains 100,000 IU/g of vitamin $D_3$.

Three batches were manufactured to evaluate the water dispersible form of vitamin $D_3$. Each batch consisted of an aqueous solution containing potassium benzoate, citric acid, sodium citrate, aspartame, calcium glycerophosphate and the water dispersible form of vitamin $D_3$. The resultant product was not homogenized. The final pH of each batch is presented in Table 7. This pH difference, however, did not seem to affect vitamin $D_3$ recovery.

TABLE 7

| BATCH | pH |
|---|---|
| 1 | 3.50 |
| 2 | 4.19 |
| 3 | 4.97 |

The initial processing losses for batches 1–3 was severe (mean=45.4% Recovery—Table 6). The loss of vitamin $D_3$ was primarily due to: (a) the fact that the vitamin $D_3$ was not homogenized into the product matrix; and (b) there was no emulsifier present that would assist in maintaining the vitamin $D_3$ in solution. Therefore, the vitamin $D_3$ was lost by the coating of the manufacturing equipment with vitamin $D_3$. The stability of Vitamin $D_3$ in these three batches was not acceptable over the shelf life of the product. As shown in Table 8, one half of the initial vitamin $D_3$ was lost in approximately 12.6 days.

TABLE 8

VITAMIN $D_3$ (IU/KG OF PRODUCT) VERSUS DAYS

| BATCH | 1 | 2 | 3 |
|---|---|---|---|
| Days[1] | | | |
| 0[2] | 440 | 405 | 450 |
| 7[2] | 328 | 315 | 347 |
| 13 | 191 | 210 | 225 |

TABLE 8-continued

VITAMIN $D_3$ (IU/KG OF PRODUCT) VERSUS DAYS

| BATCH | 1 | 2 | 3 |
|---|---|---|---|
| Corr. Coef. | 0.955 | 0.968 | 0.965 |
| $[D_o]$ | 462 | 418 | 466 |
| k | 0.0636 | 0.0501 | 0.0529 |
| $t_{1/2}$ | 10.9 | 13.8 | 13.1 |

Average Half Life ($t_{1/2}$) of Vitamin $D_3$ for Batches 1–3 is 12.6 Days
[1]Days after initial vitamin $D_3$ testing. 0-time testing occurred 7 days after the product was manufactured.
[2]Results for batches 1–3 were corrected via control value on day 0 and day 7.

b. Use of Polysorbate 80 as an Emulsifier

A series of experiments were conducted using vitamin $D_3$ in Polysorbate 80 manufactured to selected specifications by Vitamins Inc., Chicago, Ill., U.S.A. Polysorbate 80 is a water soluble, non-ionic emulsifier used for various applications in the food industry. It is a polyoxyethylene derivative of sorbitan monooleate which interacts with the oil and aqueous phases in an emulsion to form a barrier at the interface that causes a reduction in Van der Waals forces and an improvement in emulsion stability. It was expected that the use of Polysorbate 80 to incorporate the vitamin $D_3$ would improve its recovery and stability by causing dispersion of the oil phase in the continuous aqueous phase.

The effect of Polysorbate 80 was evaluated in three experimental batches of a low pH beverage. Liquid beverage concentrates were prepared as described above, i.e., adding to water sodium benzoate (instead of potassium benzoate as a preservative), citric acid, potassium citrate, aspartame, calcium glycerophosphate, and vitamin $D_3$ in a premix containing Polysorbate 80 and propylene glycol. The resultant liquid beverage concentrates were not homogenized and were diluted with five parts of water before carbonation. The vitamin $D_3$ fortification level for each batch was 635 IU/KG of product. All batches contained vitamin C. The variables in batches 4–6 are presented in Table 9. These variables were added in an attempt to improve vitamin C stability, since it has been found that cysteine, when added in a carefully controlled amount can overcome vitamin C deterioration in packaged beverages (U.S. Pat. No. 3,958,017, May 18, 1976).

TABLE 9

| BATCH | VARIABLE |
|---|---|
| 4 | Cysteine, 1.5% of Vit. C |
| 5 | No Cysteine |
| 6 | Cysteine + 250 PPM WPC |

The overall mean % Recovery for batches 4–6 was comparable to the previous batches containing the water dispersible form of vitamin $D_3$. The mean % Recovery was 43.4% (Table 6). However, as shown in Table 10, the stability of these batches improved significantly. The half life of vitamin $D_3$ in these batches ranged from 257 days to 1,160 days. Cysteine addition did not affect vitamin $D_3$ recovery, but batch 6 with whey protein concentrate (WPC) showed minimal loss of vitamin $D_3$ during 60 days of shelf life.

In addition, batch 6 also had slightly better initial vitamin $D_3$ Recovery than those batches in this series without protein. This suggested that a more rugged emulsion and some sort of matrix was needed as shown in Table 10. The use of WPC is not indicated if the product of the invention is desired to be low in calories or free of calories, but otherwise may be used in the practice of the invention. In an attempt to make a low calorie or calorie free product, the use of mechanical means such as homogenization was investigated.

TABLE 10

VITAMIN $D_3$ (IU/KG OF PRODUCT) VERSUS DAYS

| BATCH | 4 | 5 | 6 |
|---|---|---|---|
| Days[1] | | | |
| 0 | 249 | 283 | 294 |
| 7 | 226 | 272 | 282 |
| 25 | 243 | 243 | 281 |
| 60 | 261 | 239 | 279 |
| Corr. Coef. | 0.450 | 0.783 | 0.512 |
| $[D_o]$ | 236 | 275 | 288 |
| k | 0.0015 | 0.0027 | 0.0006 |
| $t_{1/2}$ | 462 | 257 | 1160 |

Average Half Life ($t_{1/2}$) of Vitamin $D_3$ for Batches 4–6 is 626 Days.
[1]Days after initial vitamin $D_3$ testing. 0-time testing occurred 2 days after the product was manufactured.

C. Use of Homogenization

In the next series of studies, the vitamin $D_3$/Polysorbate premix was combined with the aqueous phase and the blend was emulsified by passing it through a two-stage Gaulin-L-100 homogenizer at a given pressure. The purpose of this homogenization step is to break up, or evenly disperse, the oil phase into the aqueous phase so that the particle size of the emulsion is sufficiently small to retard coalescence of the oil phase and prevent separation. A two-stage homogenization is needed since the fine particles formed during the first stage can clump. The second stage, set at a lower pressure, is needed to break up the clumps, thereby making a more stable emulsion.

Brominated vegetable oil (BVO) and small quantities of gum arabic were added to the vitamin $D_3$/Polysorbate premix prior to homogenization. This was done to increase the specific gravity of the oil phase and avoid phase separation, or oiling-off, of the emulsion. BVO is used in the soda industry as a stabilizer for flavoring oils used in fruit flavored beverages. BVO is a Food Additive (21, CFR 180.30) allowed in an amount not greater than 15 ppm of the finished beverage.

A series of experiments were conducted to evaluate the effect of homogenization on vitamin $D_3$ recovery and stability. In these experiments liquid beverage concentrates were prepared as described above with the exception of the vitamin $D_3$ addition. All the water soluble components were first dissolved in water and a vitamin $D_3$ emulsion, prepared separately, was added at 1% of finished product concentration, and mixed thoroughly. The vitamin $D_3$ emulsion was prepared by combining water, vitamin $D_3$ and one or more of the following ingredients: Brominated Vegetable Oil (BVO), Polysorbate 80, Gum Arabic (GA), and corn oil, followed by homogenization using a two stage homogenizer. Two different sources of vitamin $D_3$ were used: (a) an oil soluble vitamin premix where the vitamin $D_3$ is dissolved in a small amount of corn oil; and (b) a vitamin $D_3$ premix where the vitamin $D_3$ is dissolved in Polysorbate 80 and propylene glycol (PG) (same as batches 4 through 6). One part of the complete concentrate was then dissolved with five parts of water before carbonation. The variables in batches 7–24 are presented in Table 11.

TABLE 11

| Batch | Variable (ppm = ppm of product) |
|---|---|
| 7 | BVO, Vitamin $D_3$ in Corn Oil, GA (0.14 ppm) |
| 8 | BVO, Corn oil, Vitamin $D_3$ in Polysorbate 80, GA (0.14 ppm) |
| 9 | BVO, Corn Oil, Vitamin $D_3$ in Polysorbate 80 |
| 10 | BVO, Vit $D_3$ in Corn Oil, Polysorbate 80 (0.07 ppm), GA (0.14 ppm) |
| 11 | BVO, Vit $D_3$ in Corn Oil, Polysorbate 80 (0.035 ppm), GA (0.14 ppm) |
| 12 | BVO, Vit $D_3$ in Corn Oil, Polysorbate 80 (0.035 ppm), PG (0.15 ppm), GA (0.14 ppm) |
| 13 | BVO, Vit $D_3$ in Corn Oil, Polysorbate 80 (0.07 ppm), GA (0.14 ppm) |
| 14 | BVO, Vit $D_3$ in Corn Oil, Polysorbate 80 (0.07 ppm), PG (0.30 ppm) |
| 15 | BVO, Vit $D_3$ in Corn Oil, Polysorbate 80 (0.035 ppm) |
| 16 | BVO, Vit $D_3$ in Corn Oil, Polysorbate 80 (0.035 ppm), PG (0.15 ppm) |
| 17 | BVO, Vit $D_3$ in Corn Oil, Polysorbate 80 (0.07 ppm) |
| 18 | Same as 11 |
| 19 | Same as 22 |
| 20 | Same as 13 |
| 21 | Same as 15 |
| 22 | Same as 16 |
| 23 | Same as 17 |
| 24 | BVO; Vit $D_3$ in Corn Oil, Polysorbate 80 (0.07 ppm), Fructose (42,000 ppm) |

The gum arabic used in all batches was Nutriloid Gum Arabic from Tic Gums, Inc. When extra Polysorbate 80 was added to the batches, the percent addition refers to percent of oil in the batch. Batches contain either 3% or 6% extra Polysorbate 80 added. The 20% and 40% refer to combinations of Polysorbate 80 and Propylene glycol where the Polysorbate 80 content is 3% and 6%. Fructose was added to batch number 24 to see if it would extend the shelf-life of the product which is limited by the degradation of aspartame. In general, the fructose and the various levels of Polysorbate 80 did not affect the vitamin $D_3$ recovery as the homogenization step did.

The initial vitamin $D_3$ Recovery (mean=59.4%) and the mean half-life value (150 days) for batches 7–9, as presented in vitamin $D_3$ Recovery Table 6 and Table 12, indicated that with few exceptions, the homogenization step significantly improved the initial recovery and stability of vitamin $D_3$ versus previous attempts.

TABLE 12

VITAMIN $D_3$ (IU/KG OF PRODUCT) VERSUS DAYS

| BATCH | 7 | 8 | 9 |
|---|---|---|---|
| Days[1] | | | |
| 0 | 371 | 328 | 308 |
| 7 | 354 | 372 | 346 |
| 26 | 217 | 235 | 224 |
| 70 | 189 | 284 | 236 |
| Corr. Coef. | 0.816 | 0.224 | 0.506 |
| $[D_o]$ | 349 | 324 | 309 |
| k | 0.0098 | 0.0030 | 0.0047 |
| $t_{1/2}$ | 71 | 231 | 147 |

Average Half Life ($t_{1/2}$) Of Vitamin $D_3$ for batches 7–9 is 150 days.
[1] Days after initial vitamin $D_3$ testing. 0-time testing occurred 8 days after the product was manufactured.

The vitamin $D_3$ results for batches 10–17 confirmed that homogenization was necessary. The mean % Recovery for these batches dramatically improved to 76.7% versus all previous batches (Table 6). The overall vitamin $D_3$ stability (mean half-life=68.6 days) for batches 10–17, as presented in Table 13, was not as good as batches 7–9 (150 days) but was superior in comparison to batches 1–3 (12.6 days).

TABLE 13

VITAMIN $D_3$ (IU/KG OF PRODUCT) VERSUS DAYS

| BATCH | 10 | 11 | 12 | 13 | 14 | 15 | 16 | 17 |
|---|---|---|---|---|---|---|---|---|
| Days[1] | | | | | | | | |
| 0 | 548 | 696 | 680 | 691 | 546 | 649 | 679 | 681 |
| 10 | | | 484 | 469 | | | | 478 |
| 32 | 451 | 456 | 437 | 403 | 302 | 445 | 467 | 441 |
| 57 | 250 | 382 | 351 | 321 | 228 | 355 | 358 | 342 |
| 91 | 171 | 269 | 271 | 225 | 175 | 297 | 303 | 274 |
| Corr. Coef. | 0.953 | 0.988 | 0.931 | 0.948 | 0.956 | 0.966 | 0.963 | 0.919 |
| $[D_o]$ | 591 | 672 | 598 | 602 | 497 | 615 | 645 | 594 |
| k | 0.0136 | 0.0102 | 0.0090 | 0.0111 | 0.0124 | 0.0086 | 0.0090 | 0.0090 |
| $t_{1/2}$ | 51.0 | 67.9 | 77.0 | 62.4 | 55.9 | 80.6 | 77.0 | 77.0 |

Average Half Life ($t_{1/2}$) of Vitamin $D_3$ for batches 10–17 is 68.6 days.
[1] Days after initial vitamin $D_3$ testing. 0-time testing occurred 4 days after the product was manufactured.

In order to confirm the initial vitamin $D_3$ Recovery and stability of batches 10–17, duplicate batches were made (see batches 18–19 and 21–24 in Tables 6 and 14). The initial vitamin $D_3$ Recovery for batches 18–19 and 21–24 (mean= 78.2%) corroborated previous recoveries for batches 10–17. Furthermore, the vitamin $D_3$ stability of batches 18–19 and 21–24 (mean half-life=76.7 days) was comparable to their respective duplicate batches (68.6 days).

TABLE 14

| | VITAMIN $D_3$ (IU/KG OF PRODUCT) VERSUS DAYS | | | | | | |
|---|---|---|---|---|---|---|---|
| BATCH | 18 | 19 | 20 | 21 | 22 | 23 | 24 |
| Days[1] | | | | | | | |
| 0 | 752 | 678 | 802 | 784 | 491 | 796 | 798 |
| 18 | 586 | 491 | 584 | 571 | 357 | 585 | 577 |
| 63 | 379 | 309 | 358 | 381 | 245 | 372 | 406 |
| 84 | 366 | 303 | 342 | 365 | 214 | 341 | 370 |
| Corr. Coef. | 0.958 | 0.938 | 0.954 | 0.942 | 0.969 | 0.967 | 0.951 |
| $[D_o]$ | 714 | 627 | 747 | 725 | 458 | 746 | 738 |
| k | 0.0088 | 0.0097 | 0.0103 | 0.0090 | 0.0095 | 0.0100 | 0.0088 |
| $t_{1/2}$ | 78.8 | 71.5 | 67.3 | 77.0 | 73.0 | 69.3 | 78.8 |

Average Half Life ($t_{1/2}$) of Vitamin $D_3$ is 74.7 Days. (Batch 20 is control and is not included in the average.
[1]Days after initial vitamin $D_3$ testing. 0-time testing occurred 1 day after the product was manufactured.

Although the shelf life data for batches 10–17 and 18–24 showed a loss of vitamin $D_3$ as a function time, no significant amount of degradation product could be analytically detected. Therefore, the main mechanism for loss was assumed to be physical migration of vitamin $D_3$ to the walls of the container, and/or rapid oxidation of vitamin $D_3$ and/or isomerization of vitamin $D_3$ to 5,6-trans-vitamin $D_3$. Further studies focused on increasing the emulsion stability to prevent the migration of the hydrophobic vitamin $D_3$ to the container walls.

d. Use of Gum(s) as an Emulsion Stabilizer

The use of gum arabic and gum tragacanth as emulsifying agents for flavor oils in soft drinks is well established in the soft drink industry. Melillo, "Physical Factors Governing the Stabilization of Cloudy Beverages", FOOD PRODUCTS DEVELOPMENT, June, 1977, pp. 108–110. While only gum arabic was used in the experiments, examples and prototypes disclosed herein, it is understood that one skilled in the art could substitute appropriate amounts of gum tragacanth, xanthan gum or any other appropriate gum into the products of the present invention, or that mixtures of gums may be used in the practice of the present invention.

Gum tragacanth is the dried, gummy exudation obtained from *Astragalus gummifer* or other Asiatic species of Astralagus. Tragacanth swells rapidly in either cold or hot water to a viscous colloidal sol or semi-gel. The molecular weight of the gum is on the order of 840,000 and the molecules are elongated (4500A by 19A) which accounts for its high viscosity. Tragacanth gum is compatible with other plant hydrocolloids as well as carbohydrates, most proteins, and fats. Viscosity is most stable at pH 4 to 8 with a very good stability down to pH 2.

Xanthan gum is an exocellular heteropolysaccharide produced by a distinct fermentation process. The bacterium *xanthornonas campestris* generates the gum on specific organelles at the cell surface by a complex enzymatic process. The molecular weight for xanthan gum is about two million.

Gum arabic, also known as gum acacia, is the dried, gummy exudate from the stems or branches of *Acacia senegal* or of related species of Acacia. The most unusual property of gum arabic among the natural gums is its extreme and true solubility in cold or hot water. Gum arabic is a complex calcium, magnesium, and potassium salt of arabic acid. It has a main backbone chain of (1→3)—linked D-galactopyranose units, some of which are substituted at the C-6 position with various side chains. The side chains consist of D-galactopyranose, D-glucuronic acid and L-arabofuranose with additional side chains on the D-galactopyranose of L-rhamnopyranose. The molecular weight is on the order of 250,000.

Gum Arabic is effective in stabilizing emulsions and inhibiting coalescence or phase separation by two mechanisms: (a) increasing the viscosity of the continuous (aqueous) phase; and, (b) forming strong films around the oil droplets. A small amount of protein is present in the gum arabic as a part of the structure.

A series of experiments were conducted to evaluate various types of gum arabic as the emulsifier system in the vitamin $D_3$ emulsion. Although gum arabic had been evaluated in previous experiments, the usage rate was too low (0.14 ppm) to have a significant effect. It has been reported that the proteinaceous component is responsible for gum arabic's emulsifying and stabilizing properties. The variables in batches 25–30 are presented in Table 15.

TABLE 15

| Batch | Variable |
|---|---|
| 25 | Gellan Gum, Kelco Products, 100 ppm (in beverage) |
| 26 | Gum Arabic, Tic Bev 202, Tic Gums Inc., 2000 ppm (in beverage) |
| 27 | Gum Arabic EMULGUM, Colloids Naturels Inc., 500 ppm (in beverage) |
| 28 | Gum Arabic Nutriloid, Tic Gums Inc., 2000 ppm (in beverage) |
| 29 | Control, Same as Batches 13 and 20 |
| 30 | Gum Arabic SPRAY BE, Colloid Naturels, Inc., 500 ppm (in beverage) |

Batches were prepared to evaluate the stability of various vitamin $D_3$ emulsions in finished beverages. The individual emulsions, prepared separately, were added to beverage concentrates in amounts to yield 1% by weight in the finished beverages. The emulsions themselves contained 1–20% by weight of the appropriate gums which were first hydrated in aqueous solutions for about two hours at 60° C. (See Table 15 for gums and quantities) The hydrated gum solutions were cooled to 37.8° C. or less before the needed amounts of vitamin $D_3$ were added. The type of vitamin $D_3$ used was liquid vitamin $D_3$ in corn oil obtained from Roche Vitamins and Fine Chemicals, a division of Hoffman-LaRoche Inc., Nutley, N.J., U.S.A. The pH of the emulsions which contained gum arabic were lowered to pH 4.0 and sodium benzoate was added to preserve the emulsions for extended use. The emulsions were then homogenized twice using a two-stage homogenizer at 1,500/600 PSI and 3,000/1,000 PSI, respectively.

For example, batch 27 contained 50 grams of EMULGUM gum arabic hydrated in 950 grams of water, and upon cooling 77.2 milligrams of liquid vitamin $D_3$ in corn oil was blended into the gum solution in an amount giving a theoretical fortification of about 825 IU/Kg of finished beverage. The emulsion was preserved by adding 0.3 g of sodium benzoate and the pH was lowered to 4.0 by adding 1.08 grams of citric acid. The performance of the different gums used, as indicated by initial vitamin $D_3$ recovery and stability over shelf-life varied (Tables 6 and 16, respectively). EMULGUM (batch 27) at 500 ppm concentration gave the best results followed by SPRAY BE, both from Colloids Naturels, Inc.

In general it can be said that significant improvements in vitamin $D_3$ stability were observed initially and during shelf-life. The most significant improvement was the stability of vitamin $D_3$ over the shelf life of the product. The average half-life of vitamin $D_3$ for these batches was 180 days. It appears that at sufficient concentration, gum arabic can coat the oil droplets containing the vitamin $D_3$ to form an emulsion that can be further stabilized by homogenization using a two-stage homogenizer.

This series of experiments demonstrated that gum arabic could be substituted for Polysorbate 80 to minimize initial processing loss and improve shelf life stability of vitamin $D_3$.

TABLE 16

VITAMIN $D_3$ (IU/KG OF PRODUCT) VERSUS DAYS

| BATCH | 25 | 26 | 27 | 28 | 29 | 30 |
|---|---|---|---|---|---|---|
| Days[1] | | | | | | |
| 0 | 473 | 526 | 539 | 633 | 517 | 576 |
| 11 | 341 | 398 | 460 | 460 | 393 | 517 |
| 32 | 316 | 322 | 435 | 473 | 347 | |
| 40 | | | | | | 471 |
| 63 | 276 | 236 | 377 | 427 | 266 | 380 |
| 92 | 209 | 284 | 355 | 378 | 298 | |
| 122 | 296 | 258 | 355 | 352 | 266 | 380 |
| Corr. Coef. | 0.539 | 0.663 | 0.866 | 0.812 | 0.740 | 0.804 |
| [$D_0$] | 385 | 426 | 494 | 548 | 433 | 539 |
| k | 0.0041 | 0.0051 | 0.0032 | 0.0039 | 0.0046 | 0.0035 |
| $t_{1/2}$ | 169 | 136 | 217 | 178 | 151 | 198 |

Average Half Life ($t_{1/2}$) of Vitamin $D_3$ for batches 25–28 & 30 is 190 Days. (Batch 29 is a control and is not included in average.)
[1]Days after initial vitamin $D_3$ testing. 0-time testing occurred 7 days after the product was manufactured.

BATCH 31 e. Use of Commercially Manufactured Vitamin $D_3$ Emulsion

In order to evaluate if a suitable vitamin $D_3$ emulsion could be manufactured on a larger scale, which would support commercialization of a product according to the invention, a decision was made to have the vitamin $D_3$ emulsion manufactured by an outside contractor. Tastemaker, Inc. of Cincinnati, Ohio, U.S.A., which is a provider of flavoring products, provided as a special order a vitamin $D_3$ emulsion containing water, gum arabic, partially hydrogenated soybean oil, citric acid, sodium benzoate and vitamin $D_3$. By actual analysis, this commercially manufactured vitamin $D_3$ emulsion contains, per 10 Kg: (a) about 9.52 Kg of water; (b) about 0.35 Kg of gum arabic; (c) about 0.10 Kg of partially hydrogenated soybean oil; (d) about 0.02 Kg of citric acid; (e) about 0.01 Kg of sodium benzoate; and (f) and at least about 787,000 IU of vitamin $D_3$. Tastemaker considers the manufacturing procedure it used to be proprietary to it, and did not make that information available. While the commercially manufactured emulsion contained partially hydrogenated soybean oil, and the self-manufactured emulsion contained corn oil, (see description of batches 25–30) it is understood that the invention may be practiced using any suitable vegetable oil. Batches, of which batch 31 is typical, were manufactured as described in previous experiments. The commercially manufactured vitamin $D_3$ emulsion was added to the liquid beverage concentrate in an amount to equal 1%, by weight of the finished beverage. The beverage concentrate was then added to water at a ratio of 1:5 and carbonated.

The initial vitamin $D_3$ loss for batch 31 was minimal (94.1% recovery) which had surpassed all batches to date. Furthermore, the vitamin $D_3$ stability of this batch was superior to all previous batches. As presented in Table 17 the half life of vitamin $D_3$ was 1,390 days.

TABLE 17

VITAMIN $D_3$ (IU/KG OF PRODUCT) VERSUS DAYS

| BATCH | 31 |
|---|---|
| Days[1] | |
| 0 | Not Tested |
| 23 | 763 |
| 52 | 793 |
| 87 | 742 |
| Corr. Coef. | 0.218 |
| [$D_0$] | 786 |
| k | 0.0005 |
| $t_{1/2}$ | 1,390 days |

[1]Days after product manufacture, with day 0 being the day on which the product was manufactured.

Acidulants. Acids are commonly used in food and beverages to impart specific tart or sour tastes and to function as preservatives. A combination of citric and lactic acids are used in the liquid nutritional product of the present invention. Citric acid is the most widely used acid in fruit beverages in part because it blends well with these flavors. It is commercially manufactured by fermentation or by synthesis; either may be used in the practice of the present invention. When using fermented lactic acid, a purified form that is free of sugar residues is recommended due to its cleaner taste and clearer appearance. Food grade lactic acid is available in aqueous and crystalline forms.

Sweetener. The sweetener used in the prototype beverages described below is aspartame, but other artificial or natural sweeteners can be used in the practice of the present invention. Artificial sweeteners that may be employed include saccharin, acesulfame-K and the like. Natural sweeteners that may be employed include sucrose, fructose, high fructose corn syrup, glucose, sugar alcohols, dextrose, maltodextrins, maltose, lactose, and the like but other carbohydrates can be used if less sweetness is desired. Mixtures of natural sweeteners, or artificial sweeteners, or natural and artificial sweeteners can be used also.

The amount of the sweetener effective in a product according to any aspect of the present invention depends upon the particular sweetener used and the sweetness intensity desired. In determining the amount of sweetener, any sugar or other sweetener present in the flavor component or product matrix should also be taken into consideration.

Studies have shown that the efficiency of calcium absorption can be enhanced two-five fold by oral administration of glucose polymer both in patents with intestinal calcium malabsorption and in normal subjects. Kelley, et al., "Effect of Meal Composition on Calcium Absorption: Enhancing Effect of Carbohydrate Polyer" *GASTROENTEROLOGY*, 87: 596–600 (1984).

In another study using the triple-lumen intestinal perfusion technique, glucose polymer increased net calcium absorption fourfold. Bei, et al., "Glucose Polymer Increases and Equal Calcium Magnesium, and Zinc Absorption in Humans", AMERICAN JOURNAL OF CLINICAL NUTRITION, 44: 244–247 (1986).

It is understood that a person of skill in the art may make a product in accordance with the invention containing glucose polymers or glucose.

Flavor. As used herein, the term "flavor" includes both natural and artificial flavors. The particular amount of the flavor component effective for imparting flavor characteristics to the beverage of the present invention can depend upon the flavor(s) selected, the flavor impression desired, and the form of the flavor component. The amount of flavor employed in a product according to any aspect of the present invention is within the skill of one in the art and depends on the flavor intensity desired.

Preservatives. Most microbial spoilage of low pH beverages is caused by aciduric and acidophilic organisms like certain varieties of yeasts and molds. For this reason, preservatives with anti-microbial activity such as benzoic and sorbic acids are added to soft drinks. Usage levels of these acids or their salts range from 0.025 to 0.050 percent, depending on the nutritive substances present and the pH of the finished beverage. The antimicrobial activity of these preservatives has been shown to be largely pH dependent. They are least effective under neutral conditions but their activity increases considerably with decreasing pH. For example, by reducing the pH value from 4.5 to 3.0, the preservative effect of benzoic acid is increased by nearly three times. Only beverages at low pH receive the full benefit from the addition of preservatives. Woodruf et al., BEVERAGES: CARBONATED AND NONCARBONATED, The AVI Publishing Company, Inc., 1974, pgs. 143–146. As with most foods, the successful preservation of low pH beverages is dependent on controlling contamination of ingredients, processing equipment, and containers by potential spoilage organisms. Splittstoesser in FOOD AND BEVERAGE MYCOLOGY, edited by Beuchatt, published by Van Nostrand Reinhold, 1987, pgs. 120–122.

Carbonation. The amount of carbon dioxide in a beverage according to the present invention depends upon the particular flavor system used and the amount of carbonation desired. Usually, carbonated beverages of the present invention contain from 1.0 to 4.5 volumes of carbon dioxide. Preferred carbonated beverages contain from 2 to 3.5 volumes of carbon dioxide. The beverages of the present invention can be prepared by standard beverage formulation techniques. To make a carbonated beverage carbon dioxide can be introduced either into the water mixed with the beverage syrup or into the drinkable diluted beverage to achieve carbonation. It should be understood, however, that carbonated beverage manufacturing techniques, when appropriately modified, are also applicable to noncarbonated beverages.

EMBODIMENTS OF THE INVENTION

Tables 18–21 present bills of materials for manufacturing prototypes of low pH beverages fortified with calcium and vitamin $D_3$ in accordance with some aspects of the invention.

TABLE 18

Bill of Materials for Wild Cherry Flavored Beverage (For 1000 KG of Beverage)

| INGREDIENT | AMOUNT, KG |
|---|---|
| Treated Water[1] (for beverage concentrate) | 137.82 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Wild Cherry Color | 0.000630 |
| FD&C Red #40 | 0.0003465 |
| FD&C Yellow #6 | 0.0002835 |
| Natural & Artificial Wild Cherry Flavor | 1.200 |
| Ascorbic Acid | 0.300 |
| Vitamin $D_3$ Emulsion[2] | 10.000 |
| Treated Water[1] (for final blend) | 833.33 |

[1]"treated water" has had the chlorine and alkalinity adjusted to levels commonly used in the soft drink industry.
[2]This emulsion is described above with regards to batch 31.

TABLE 19

Bill of Materials for Orange Flavored Beverage (For 1000 KG of Beverage)

| INGREDIENT | AMOUNT, KG |
|---|---|
| Treated Water[1] (for beverage concentrate) | 137.62 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Orange Color | 0.0001875 |
| FD&C Yellow #6 | 0.00140625 |
| FD&C Red #40 | 0.00046875 |
| Natural and Artificial Orange Flavor | 1.400 |
| Ascorbic Acid | 0.300 |
| Vitamin $D_3$ Emulsion[2] | 10.000 |
| Treated Water[1] (for final blend) | 833.33 |

[1]"treated water" had had the chlorine, and alkalinity adjusted to levels commonly used in the soft drink industry.
[2]This emulsion is described above with regards to batch 31.

TABLE 20

Bill of Materials For Peach Flavored Beverage (For 1000 KG of Beverage)

| INGREDIENT | AMOUNT, KG |
|---|---|
| Treated Water[1] (for beverage concentrate) | 137.42 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Mohawk Casing Color | 0.001250 |
| FD&C Yellow #6 | 0.0008125 |
| FD&C Red #40 | 0.0004375 |
| Natural and Artificial Peach Flavor | 1.600 |
| Ascorbic Acid | 0.300 |
| Vitamin $D_3$ Emulsion[2] | 10.000 |

TABLE 20-continued

Bill of Materials For Peach Flavored Beverage (For 1000 KG of Beverage)

| INGREDIENT | AMOUNT, KG |
| --- | --- |
| Treated Water[1] (for final blend) | 833.33 |

[1]"treated water" has had the chlorine and alkalinity adjusted to levels commonly used in the soft drink industry.
[2]This emulsion is described above with regards to batch 31.

TABLE 21

Bill of Materials For Lemon Lime Flavored Beverage (For 1000 KG of Beverage)

| INGREDIENT | AMOUNT, KG |
| --- | --- |
| Treated Water[1] (for beverage concentrate) | 138.02 |
| Potassium Benzoate | 0.300 |
| Sodium Citrate (dihydrate) | 0.550 |
| Citric Acid (anhydrous) | 3.720 |
| Lactic Acid (88%) | 3.951 |
| Aspartame | 0.500 |
| Calcium Glycerophosphate | 8.331 |
| Lemon Lime Color | 0.000630 |
| FD&C Yellow #5 | 0.0005796 |
| FD&C Green #3 | 0.0000504 |
| Natural and Artificial Lemon Lime Flavor | 1.000 |
| Ascorbic Acid | 0.300 |
| Vitamin $D_3$ Emulsion[2] | 10.000 |
| Treated Water[1] (for final blend) | 833.33 |

[1]"treated water" has had the chlorine and alkalinity adjusted to levels commonly used in the soft drink industry.
[2]This emulsion is described above with regards to batch 31.

EXAMPLE 1

PREPARATION OF LIQUID BEVERAGE CONCENTRATE

The concentrated mixture of ingredients that make up the beverage is referred to as the beverage concentrate. The liquid beverage concentrate comprises at least water, a source of calcium, vitamin $D_3$, gum arabic and vegetable oil. Preferably, the beverage concentrate also comprises vitamin C. If desired, the beverage concentrate may also comprise: an acidulant, preservative(s), and/or flavoring agent(s), and/or acid stable coloring agent(s). Prototypes of the beverage of the present invention have a weight ratio of total acids to calcium of about 5.1. Prototype beverages of the present invention contained vitamin $D_3$ at levels of about $1.45 \times 10^{-6}$ to about $1.75 \times 10^{-6}$% w/w, and calcium at levels of about $1.46 \times 10^{-1}$ to about $1.47 \times 10^{-1}$ w/w.

In this example the liquid beverage concentrate is prepared in a single vessel at ambient temperature by dissolving the ingredients in water using a blending tank equipped with vigorous agitation capability. A specific order of addition, shown in Table 22, is followed to aid in dispersing the ingredients in an efficient manner. Each ingredient should be completely dissolved before the next ingredient is added.

TABLE 22

1. Water
2. Potassium Benzoate
3. Sodium Citrate
4. Citric Acid
5. Lactic Acid
6. Aspartame
7. Calcium Glycerophosphate
8. Acid Stable Coloring Agent(s)
9. Natural and Artificial Flavor(s) Agent(s)
10. Ascorbic Acid
11. Vitamin $D_3$ Emulsion (vitamin $D_3$ +gum arabic)

In commercial beverage manufacturing, it is common for beverage concentrates to be prepared a day or more (often weeks or months) in advance of blending and filling containers with the final product. For this reason, the vitamin components may be added to the liquid beverage concentrate just prior to blending with water to complete the beverage in order to prevent unnecessary long term exposure to air.

EXAMPLE 2

PREPARATION Of LIQUID BEVERAGE CONCENTRATE

Variations to the beverage concentrate manufacturing procedure described in EXAMPLE 1 can be made if available mixing vessel sizes are limited and no single mixing vessel is able to contain the required volume of beverage concentrate. Beverages according to the present invention have been manufactured by preparing a plurality of beverage concentrate component slurries which were thereafter combined by pumping each beverage concentrate component slurry to a larger sized tank. The water was divided equally between five different beverage concentrate component slurries, all of which were constantly agitated. A first beverage concentrate component slurry was made by first adding potassium benzoate and then sodium citrate to the water. A second beverage concentrate component slurry was made by adding to the water in the following order: (a) citric acid; (b) lactic acid: (c) aspartame; (d) calcium glycerophosphate. A third beverage concentrate component slurry was made by adding the acid stable coloring agent(s) and then the flavoring agent(s) to the water. A fourth beverage concentrate component slurry was made by adding the ascorbic acid to the water. A fifth beverage concentrate component slurry was made by adding the vitamin $D_3$ emulsion to the water. The beverage concentrate component slurries are transferred to a single larger sized vessel in the order in which they have been described. The resultant blend (the beverage concentrate) in the larger sized vessel was vigorously agitated for not longer than about two minutes to homogeneously blend the beverage concentrate component slurries together. A liquid beverage concentrate in accordance with the invention should have a pH of 2.8–4.6, preferably 3.1–3.8. The pH of the prototype beverage concentrates typically ranges from 3.1–3.8. If necessary, additional lactic acid is used to adjust the pH of the beverage concentrate to this range.

EXAMPLE 3

PREPARATION Of CARBONATED BEVERAGE

Deareation and cooling increases the beverage's carbonation efficiency and stability because the solubility of carbon dioxide in water is directly proportional to carbon dioxide pressure and inversely proportional to temperature. The extent of carbonation is expressed in terms of carbon dioxide gas volumes. The number of volumes can be determined by comparing sample readings with carbon dioxide temperature/pressure relationship charts. Since pressure gauges measure the sum of pressures from all gases, the presence of air in the carbonated mix can cause errors in $CO_2$ volume determination unless corrections are made. A Zahm & Nagel air tester makes it possible to easily measure the pressure and air content of a sample. To make such a test, the sample container is pierced, allowing head space gases to be released into a buret filled with 10–20% sodium or potassium hydroxide. The carbon dioxide is absorbed by the basic solution, leaving only air inside the burette. The total pressure reading is then corrected for the amount of air present in the burette, resulting in the corrected $CO_2$ pressure. The gas volumes of the sample are then determined using the corrected pressure.

A beverage in accordance with the invention may be carbonated by either blending the beverage concentrate with carbonated water or blending the beverage concentrate with water followed by carbonation of the blend. The prototype beverages were manufactured using a 5 to 1 ratio of beverage concentrate manufactured according to Example 2 to non-carbonated water. Carbonation levels in the finished beverage may range from about 1.0–4.5 volumes of $CO_2$, depending on flavor or desired sensory attributes. The product is then packaged and sealed in aluminum cans or tinted glass bottles. During the production of the prototype beverages, separate in-stream lines of beverage concentrate and water were combined in the proper ratio by a continuous metering device known in the art as a volumetric proportioner and then deaerated. The resulting mixture was transferred to a carbo-cooler where it was cooled and carbonated to approximately 2.5 volumes. The pH of the finished beverage should be in the range of about 3.1–4, and the pH of the prototypes was about 3.7. The finished product was then filled into standard 12 oz. aluminum soda cans.

The nutritional profile and initial vitamin $D_3$ Recoveries of the prototype low pH beverages in accordance with the invention are presented in Tables 23 and 24.

TABLE 23

NUTRITIONAL PROFILE OF PROTOTYPE BEVERAGE
SERVING SIZE 1 CAN (355 mL)

| | AMOUNT PER SERVING | % Daily Value* |
|---|---|---|
| Calories | 0 | |
| Total Fat | 0 g | 0% |
| Sodium | 45 mg | 2% |
| Potassium | 25 mg | 1% |
| Total Carbohydrate | 0 g | 0% |
| Protein | 0 g | 0% |
| Vitamin C 50% of RDI | | |
| Calcium 50% of RDI | | |
| Vitamin D 30% of RDI | | |

*Not a significant source of other nutrients.
*Percent Daily Values are based on a 2,000 calorie diet;

TABLE 24

VITAMIN $D_3$ (IU/KG OF PRODUCT)
(THEORETICAL FORTIFICATION AT 810 IU/KG OF PRODUCT)

| FLAVOR | 0-TIME | % RECOVERY |
|---|---|---|
| Cherry | 597 | 73.7 |
| Lemon Lime | 613 | 75.7 |
| Peach | 701 | 86.6 |
| Orange | 580 | 71.6 |

Average = 76.9% vitamin $D_3$ Recovery

EXAMPLE 4

CARBONATED BEVERAGE

An alternative embodiment of a liquid beverage concentrate may be prepared according to Example 1 or Example 2 excluding any ingredients other than the water, calcium source, vitamin $D_3$ and gum arabic (eg. the flavorant, and/or the colorant, and/or the sweetener may be omitted). This liquid beverage concentrate may then be combined with another liquid beverage concentrate, such as a commercial soda pop concentrate, and the resultant blended beverage concentrate may thereafter be combined with carbonated water, or combined with non-carbonated water with the resultant beverage being carbonated in the manner described above in Example 3.

EXAMPLE 5

NON-CARBONATED BEVERAGE

A liquid beverage concentrate may be prepared by blending a liquid beverage concentrate according to the present invention, such as described above in Examples 1 and 2, with non-carbonated water. The resultant blend could then be placed into aluminum soda cans, or light reducing bottles, the head space flushed with nitrogen gas or carbon dioxide to eliminate oxygen which is harmful to vitamin and color stability, and sealing the cans in the usual manner.

EXAMPLE 6

NON-CARBONATED BEVERAGE

An alternative embodiment of a liquid beverage concentrate may be prepared according to Example 1 or Example 2 excluding any ingredients other than the water, calcium source, vitamin $D_3$ and gum arabic (eg. the flavorant, and/or colorant, and or sweetener could be omitted), and thereafter blending the concentrate with fruit juice, vegetable juice, or any other suitable liquid matrix.

EXAMPLE 7

POWDERED BEVERAGE CONCENTRATE

The bill of materials for a powdered beverage concentrate in accordance with the invention is presented in Table 25.

TABLE 25

BILL OF MATERIALS FOR POWDERED
BEVERAGE CONCENTRATE

| INGREDIENT | AMOUNT |
|---|---|
| Vitamin $D_3$ Emulsion[1] | 350 g |
| Calcium Glycerophosphate | 291.6 g |
| Lactic Acid Powder (60% lactic acid) | 151.3 g |
| Citric Acid | 130.2 g |
| Natural Cherry Flavor | 42.0 g |
| Sodium Citrate Dihydrate | 19.3 g |
| Aspartame | 17.5 g |
| Ascorbic Acid | 10.5 g |

[1]This emulsion is described above with regards to batch 31.

A powdered beverage concentrate was prepared by placing the calcium glycerophosphate, sodium citrate, citric acid, lactic acid and ascorbic acid into the chamber of an Aeromatic Top Agglomerator. The powder was then blended for two minutes under medium fluidization. The temperature was brought to 70° C., the atomization was set at 1 Bar, the atomizing nozzle was placed at the highest level of three possible positions, and the fan capacity was set initially at 12 (nominal setting).

Aspartame was dissolved in approximately 800 ml of warm tap water and a small amount of citric acid was added to achieve a pH of approximately 4. The vitamin $D_3$ emulsion and the flavor system were blended by hand with the aspartame solution to yield approximately 1200 ml of liquid. The 1200 ml of liquid was placed on a stir plate and agitated under medium agitation while being sprayed onto the fluidized powder for approximately three hours.

As the liquid was sprayed, the powder became heavy and it became necessary to increase the fan capacity to maximum and place the atomizing nozzle in the center position. Per actual analysis, a Kg of powdered beverage concentrate contained about 83.5 g of calcium, 12.9 g of vitamin C and 31,900 IU of vitamin $D_3$.

The final powder particles were relatively large and brittle and were pulverized before reconstituting with water. The powder was easily reconstituted (see Example 8) and flavor was typical of a powdered beverage concentrate product without the carbonation. Longer shelf life in this kind of beverage concentrate is anticipated because of the absence of water.

EXAMPLE 8

NON-CARBONATED BEVERAGE CONTAINING POWDERED BEVERAGE CONCENTRATE

Approximately 19.1 grams of the powdered beverage concentrate manufactured in Example 7 were dissolved in a sufficient amount of tap water to yield 1 Kg of beverage. A Kg of the resultant beverage is projected to contain about 1.4 g of calcium, about 0.25 g of vitamin C, and about 607 IU of vitamin $D_3$. As in the case of the liquid form of the powdered beverage concentrate, the acid system can vary depending on the flavor selected.

EXAMPLE 9

POWDERED BEVERAGE ADDITIVE

A powdered beverage additive may be manufactured by the process described in Example 7, containing at least vitamin $D_3$, a calcium source and vitamin C, but if desired omitting sweetener, acids, flavoring, etc. The resultant powdered beverage additive could be added in appropriate quantities to a liquid matrix such as a fruit juice, blend of fruit juices, vegetable juices, coffee, tea or any suitable beverage. The powdered beverage additive could be employed in bulk, (eg. at an orange juice processing facility), or on a serving by serving basis when provided in single serving size packets.

It should be noted that if a liquid or powdered beverage concentrate or beverage additive according to the invention is intended for use in a liquid matrix that may contain any dairy product, (for example, coffee or tea that may contain cream), a salt of ascorbic acid should be used in place of ascorbic acid to prevent curdling of the dairy product.

EXAMPLE 10

CALCIUM SUPPLEMENT

A calcium glycerophosphate/vitamin $D_3$/vitamin C tablet supplement was prepared by placing about 291.6 g of calcium glycerophosphate and about 10.5 g of ascorbic acid (vitamin C) into the chamber of an Aeromatic laboratory batch agglomerator. The powder was then blended for three minutes under medium agitation. The temperature was brought to 55° C., the atomization was set to 1 bar, the atomizing nozzle was placed at the highest of three possible positions, and the fan capacity was set initially at 9 (nominal setting).

The peristaltic pump was set at 7 cc/minute and approximately 350 g of vitamin $D_3$ emulsion was sprayed onto the fluidized powder. The commercially manufactured vitamin $D_3$ emulsion described above with respect to batch 31 was used in this calcium supplement. However, any suitable dry blendable source of vitamin D, preferably vitamin $D_3$ or $D_2$, may be used for making a solid calcium supplement according to the invention. As the liquid emulsion was sprayed, the powder became heavy and as powder fluidization was depressed the fan speed was incrementally increased to 12 over 55 minutes to maintain medium fluidization. Temperature was also increased to 60° C. after 16 minutes. After all the vitamin $D_3$ emulsion was sprayed on the powder, the heat was kept on and the powder was dried for three minutes. Per actual analysis, a Kg of powder for tableting contained about 139.9 g of calcium, 26.4 g of vitamin C, and 39,600 IU of vitamin $D_3$.

The final powder particle was a soft agglomerate. No excipients were added to the powder to facilitate the tableting process. Using a tablet die of approximately ½ inch diameter, 600 g of the final powder was compressed using a Carver model C laboratory press and an applied load of 200 pounds force. The tablet was easily removed from the die. This process was repeated using 1000 g and 1500 g of final powder to produce a total of three calcium supplement tablets, 600 g, 1000 g, and 1500 g, respectively.

A calcium supplement in solid form in accordance with the invention, comprising calcium glycerophosphate, vitamin D, and vitamin C, is believed to be advantageous over prior art calcium supplements because it provides a source of calcium that has a low aluminum content as well as providing vitamin D.

We claim:

1. A calcium supplement in solid form essentially free of carbohydrate and protein consisting essentially of claim glycerophosphate vitamin D, vegetable oil at a concentration of less than about 1.1% by wt. of said supplement, vitamin C, and a non-hydrolyzed gum selected from the group consisting of gum arabic, gum tragacanth and xanthan gum.

2. The calcium supplement of claim 1 wherein the gum is gum arabic.

3. The calcium supplement of claim 1 wherein the vegetable oil is partially hydrogenated soybean oil.

4. The calcium supplement of claim 2 wherein the vegetable oil is partially hydrogenated soybean oil.

5. The calcium supplement of claim 1 wherein the vegetable oil is corn oil.

6. The calcium supplement of claim 2 wherein the vegetable oil is corn oil.

7. A calcium supplement in solid form consisting essentially of calcium glycerophosphate vitamin D, vegetable oil at a concentration of less than about 1% by wt. of said supplement, a non-hydrolyzed gum selected from the group consisting of gum arabic, gum tragacanth and xanthan gum, wherein said supplement containing from about 5.6 to 18.00% by wt. calcium.

* * * * *